(12) United States Patent
Parish et al.

(10) Patent No.: US 8,778,005 B2
(45) Date of Patent: *Jul. 15, 2014

(54) METHOD AND SYSTEM FOR THERMAL AND COMPRESSION THERAPY RELATIVE TO THE PREVENTION OF DEEP VEIN THROMBOSIS

(75) Inventors: Overton L. Parish, Frisco, TX (US); Tony Quisenberry, Highland Village, TX (US); Niran Balachandran, Lewisville, TX (US); Sam K. McSpadden, Austin, TX (US)

(73) Assignee: ThermoTek, Inc., Flower Mound, TX (US)

( * ) Notice: Subject to any disclaimer, the term of this patent is extended or adjusted under 35 U.S.C. 154(b) by 1496 days.

This patent is subject to a terminal disclaimer.

(21) Appl. No.: 12/234,394

(22) Filed: Sep. 19, 2008

(65) Prior Publication Data

US 2009/0069731 A1   Mar. 12, 2009

Related U.S. Application Data

(63) Continuation-in-part of application No. 11/733,709, filed on Apr. 10, 2007, and a continuation-in-part of application No. 10/894,369, filed on Jul. 19, 2004, now abandoned.

(60) Provisional application No. 60/791,132, filed on Apr. 11, 2006, provisional application No. 60/817,932, filed on Jun. 30, 2006, provisional application No. 60/488,709, filed on Jul. 18, 2003, provisional application No. 60/550,658, filed on Mar. 5, 2004, provisional application No. 60/588,453, filed on Jul. 6, 2004.

(51) Int. Cl.
*A61F 7/00* (2006.01)
*A61H 9/00* (2006.01)

(52) U.S. Cl.
CPC ....... *A61F 7/0085* (2013.01); *A61H 2201/5071* (2013.01); *A61F 2007/0091* (2013.01); *A61H 2201/5082* (2013.01); *A61F 2007/0075* (2013.01); *A61H 2201/165* (2013.01); *A61H 2209/00* (2013.01); *A61F 2007/0039* (2013.01); *A61H 2205/106* (2013.01); *A61H 9/0078* (2013.01); *A61F 2007/0056* (2013.01)
USPC .......................................... 607/108; 607/104

(58) Field of Classification Search
USPC ........................................ 607/104–112, 114
See application file for complete search history.

(56) References Cited

U.S. PATENT DOCUMENTS

| 773,828 A | 11/1904 | Titus et al. |
| 2,110,022 A | 3/1938 | Kliesrath |

(Continued)

FOREIGN PATENT DOCUMENTS

| CH | 670 541 | 6/1989 |
| DE | 35 22 127 | 1/1987 |

(Continued)

OTHER PUBLICATIONS

Mahmoud Karimi Azar Daryany, et al., "Photoinactivation of *Escherichia coli* and *Saccharomyces cerevisiae* Suspended in Phosphate-Buffered Saline-A Using 266- and 355-nm Pulsed Ultraviolet Light", Curr Microbiol, vol. 56, 2008, pp. 423-428.

(Continued)

*Primary Examiner* — Aaron Roane
(74) *Attorney, Agent, or Firm* — Winstead PC

(57) ABSTRACT

A control unit coupled to a thermal therapy device, a compression therapy device and DVT therapy devices is provided. The thermal therapy device includes a fluid bladder for delivering hot and/or cold therapy to a patient. The compression therapy device includes an gas bladder for providing compression to a patient. The DVT therapy devices provide pulsed compression in coordination with the compression therapy device.

11 Claims, 14 Drawing Sheets

(56) References Cited

U.S. PATENT DOCUMENTS

| | | |
|---|---|---|
| 2,504,308 A | 4/1950 | Donkle, Jr. |
| 3,014,117 A | 12/1961 | Madding |
| 3,164,152 A | 1/1965 | Vere Nicoll |
| 3,345,641 A | 10/1967 | Jennings |
| 3,367,319 A | 2/1968 | Carter, Jr. |
| 3,548,809 A | 12/1970 | Conti |
| 3,608,091 A | 9/1971 | Olson et al. |
| 3,660,849 A | 5/1972 | Jonnes et al. |
| 3,736,764 A | 6/1973 | Chambers et al. |
| 3,738,702 A | 6/1973 | Jacobs |
| 3,744,053 A | 7/1973 | Parker et al. |
| 3,744,555 A | 7/1973 | Fletcher et al. |
| 3,862,629 A | 1/1975 | Rotta |
| 3,894,213 A | 7/1975 | Agarwala |
| 4,006,604 A | 2/1977 | Seff |
| 4,013,069 A | 3/1977 | Hasty |
| 4,029,087 A | 6/1977 | Dye et al. |
| 4,206,751 A | 6/1980 | Schneider |
| 4,224,941 A | 9/1980 | Stivala |
| 4,375,217 A | 3/1983 | Arkans |
| 4,402,312 A | 9/1983 | Villari et al. |
| 4,459,468 A | 7/1984 | Bailey |
| 4,459,822 A | 7/1984 | Pasternack |
| 4,471,787 A | 9/1984 | Bentall |
| 4,503,484 A | 3/1985 | Moxon |
| 4,547,906 A | 10/1985 | Nishida et al. |
| 4,597,384 A | 7/1986 | Whitney |
| 4,608,041 A | 8/1986 | Nielsen |
| D285,821 S | 9/1986 | Kneisley |
| D288,372 S | 2/1987 | Adams |
| 4,660,388 A | 4/1987 | Greene, Jr. |
| D295,897 S | 5/1988 | Thimm-Kelly |
| 4,741,338 A | 5/1988 | Miyamae |
| 4,821,354 A | 4/1989 | Little |
| 4,844,072 A | 7/1989 | French et al. |
| 4,884,304 A | 12/1989 | Elkins |
| 4,901,200 A | 2/1990 | Mazura |
| 4,911,231 A | 3/1990 | Horne et al. |
| 4,926,881 A | 5/1990 | Ichinomiya et al. |
| 4,962,761 A | 10/1990 | Golden |
| 4,969,881 A | 11/1990 | Viesturs |
| 4,979,375 A | 12/1990 | Nathans et al. |
| 4,989,589 A | 2/1991 | Pekanmaki et al. |
| 4,995,698 A | 2/1991 | Myers |
| 4,996,970 A | 3/1991 | Legare |
| 5,044,364 A | 9/1991 | Crowther |
| 5,051,562 A | 9/1991 | Bailey et al. |
| D320,872 S | 10/1991 | McCrane |
| 5,067,040 A | 11/1991 | Fallik |
| 5,080,089 A | 1/1992 | Mason et al. |
| 5,090,409 A | 2/1992 | Genis |
| 5,092,271 A | 3/1992 | Kleinsasser |
| 5,097,829 A | 3/1992 | Quisenberry |
| 5,106,373 A | 4/1992 | Augustine et al. |
| 5,112,045 A | 5/1992 | Mason et al. |
| 5,117,812 A | 6/1992 | McWhorter |
| 5,125,238 A | 6/1992 | Ragan et al. |
| 5,165,127 A | 11/1992 | Nicholson |
| 5,179,941 A | 1/1993 | Siemssen et al. |
| 5,184,612 A | 2/1993 | Augustine |
| 5,186,698 A | 2/1993 | Mason et al. |
| 5,230,335 A | 7/1993 | Johnson, Jr. et al. |
| 5,232,020 A | 8/1993 | Mason et al. |
| 5,241,951 A | 9/1993 | Mason et al. |
| 5,243,706 A | 9/1993 | Frim et al. |
| 5,263,538 A | 11/1993 | Amidieu et al. |
| 5,285,347 A | 2/1994 | Fox et al. |
| D345,082 S | 3/1994 | Wenzl |
| D345,609 S | 3/1994 | Mason et al. |
| D345,802 S | 4/1994 | Mason et al. |
| D345,803 S | 4/1994 | Mason et al. |
| 5,300,101 A | 4/1994 | Augustine et al. |
| 5,300,102 A | 4/1994 | Augustine et al. |
| 5,300,103 A | 4/1994 | Stempel et al. |
| 5,303,716 A | 4/1994 | Mason et al. |
| 5,316,250 A | 5/1994 | Mason et al. |
| D348,106 S | 6/1994 | Mason et al. |
| 5,323,847 A | 6/1994 | Koizumi et al. |
| 5,324,319 A | 6/1994 | Mason et al. |
| 5,324,320 A | 6/1994 | Augustine et al. |
| D348,518 S | 7/1994 | Mason et al. |
| 5,330,519 A | 7/1994 | Mason et al. |
| 5,336,250 A | 8/1994 | Augustine |
| 5,343,579 A | 9/1994 | Dickerhoff et al. |
| 5,350,417 A | 9/1994 | Augustine |
| D351,472 S | 10/1994 | Mason et al. |
| 5,352,174 A | 10/1994 | Mason et al. |
| 5,354,117 A | 10/1994 | Danielson et al. |
| D352,781 S | 11/1994 | Mason et al. |
| 5,360,439 A | 11/1994 | Dickerhoff et al. |
| 5,370,178 A | 12/1994 | Agonafer et al. |
| 5,371,665 A | 12/1994 | Quisenberry et al. |
| D354,138 S | 1/1995 | Kelly |
| D357,747 S | 4/1995 | Kelly |
| 5,402,542 A | 4/1995 | Viard |
| 5,405,370 A | 4/1995 | Irani |
| 5,405,371 A | 4/1995 | Augustine et al. |
| 5,407,421 A | 4/1995 | Goldsmith |
| D358,216 S | 5/1995 | Dye |
| 5,411,494 A | 5/1995 | Rodriguez |
| 5,411,541 A | 5/1995 | Bell et al. |
| 5,417,720 A | 5/1995 | Mason |
| 5,440,450 A | 8/1995 | Lau et al. |
| 5,449,379 A | 9/1995 | Hadtke |
| 5,466,250 A | 11/1995 | Johnson, Jr. et al. |
| 5,496,262 A | 3/1996 | Johnson, Jr. et al. |
| 5,505,726 A | 4/1996 | Meserol |
| 5,507,792 A | 4/1996 | Mason et al. |
| 5,509,894 A | 4/1996 | Mason et al. |
| 5,528,485 A | 6/1996 | Devilbiss et al. |
| 5,561,981 A | 10/1996 | Quisenberry et al. |
| 5,566,062 A | 10/1996 | Quisenberry et al. |
| D376,013 S | 11/1996 | Sandman et al. |
| 5,578,022 A | 11/1996 | Scherson et al. |
| 5,588,954 A | 12/1996 | Ribando et al. |
| 5,591,200 A | 1/1997 | Cone et al. |
| D380,874 S | 7/1997 | Caswell |
| 5,648,716 A | 7/1997 | Devilbiss et al. |
| D383,546 S | 9/1997 | Amis et al. |
| D383,547 S | 9/1997 | Mason et al. |
| D383,848 S | 9/1997 | Mason et al. |
| 5,662,695 A | 9/1997 | Mason et al. |
| 5,672,152 A | 9/1997 | Mason et al. |
| 5,675,473 A | 10/1997 | McDunn et al. |
| 5,682,748 A | 11/1997 | DeVilbiss et al. |
| 5,689,957 A | 11/1997 | DeVilbiss et al. |
| 5,690,849 A | 11/1997 | DeVilbiss et al. |
| 5,711,029 A | 1/1998 | Visco et al. |
| 5,711,155 A | 1/1998 | DeVilbiss et al. |
| D393,073 S | 3/1998 | Downing et al. |
| 5,731,954 A | 3/1998 | Cheon |
| 5,733,321 A | 3/1998 | Brink |
| D394,707 S | 5/1998 | Tsubooka |
| 5,755,755 A | 5/1998 | Panyard |
| 5,772,618 A | 6/1998 | Mason et al. |
| 5,782,780 A | 7/1998 | Mason et al. |
| 5,795,312 A | 8/1998 | Dye |
| 5,807,294 A | 9/1998 | Cawley et al. |
| 5,827,208 A | 10/1998 | Mason et al. |
| 5,831,824 A | 11/1998 | McDunn et al. |
| D403,779 S | 1/1999 | Davis et al. |
| D404,490 S | 1/1999 | Tripolsky |
| D405,884 S | 2/1999 | Roper |
| 5,871,526 A | 2/1999 | Gibbs et al. |
| 5,890,371 A | 4/1999 | Rajasubramanian et al. |
| 5,901,037 A | 5/1999 | Hamilton et al. |
| 5,923,533 A | 7/1999 | Olson |
| 5,947,914 A | 9/1999 | Augustine |
| 5,980,561 A | 11/1999 | Kolen et al. |
| 5,989,285 A * | 11/1999 | DeVilbiss et al. ............ 607/107 |
| 6,007,559 A | 12/1999 | Arkans |
| 6,055,157 A | 4/2000 | Bartilson |
| 6,058,010 A | 5/2000 | Schmidt et al. |
| 6,058,712 A | 5/2000 | Rajasubramanian et al. |

(56) References Cited

U.S. PATENT DOCUMENTS

| | | |
|---|---|---|
| 6,080,120 A | 6/2000 | Sandman et al. |
| D428,153 S | 7/2000 | Davis |
| D430,288 S | 8/2000 | Mason et al. |
| D430,289 S | 8/2000 | Mason et al. |
| 6,117,164 A | 9/2000 | Gildersleeve et al. |
| 6,125,036 A | 9/2000 | Kang et al. |
| 6,129,688 A | 10/2000 | Arkans |
| 6,135,116 A | 10/2000 | Vogel et al. |
| 6,176,869 B1 | 1/2001 | Mason et al. |
| 6,186,977 B1 | 2/2001 | Andrews et al. |
| 6,238,427 B1 | 5/2001 | Matta |
| 6,260,890 B1 | 7/2001 | Mason |
| 6,270,481 B1 | 8/2001 | Mason et al. |
| 6,295,819 B1 | 10/2001 | Mathiprakasam et al. |
| 6,305,180 B1 | 10/2001 | Miller et al. |
| 6,319,114 B1 | 11/2001 | Nair et al. |
| 6,352,550 B1 | 3/2002 | Gildersleeve et al. |
| 6,358,219 B1 | 3/2002 | Arkans |
| 6,368,592 B1 | 4/2002 | Colton et al. |
| 6,436,064 B1 | 8/2002 | Kloecker |
| 6,443,978 B1 | 9/2002 | Zharov |
| 6,462,949 B1 | 10/2002 | Parish, IV et al. |
| 6,468,237 B1 | 10/2002 | Lina |
| 6,508,831 B1 | 1/2003 | Kushnir |
| D472,322 S | 3/2003 | Hoglund et al. |
| D473,315 S | 4/2003 | Miros et al. |
| D473,656 S | 4/2003 | Miros et al. |
| D473,948 S | 4/2003 | Elkins et al. |
| 6,551,264 B1 | 4/2003 | Cawley et al. |
| D474,544 S | 5/2003 | Hoglund et al. |
| 6,562,060 B1 | 5/2003 | Momtaheni |
| 6,596,016 B1 | 7/2003 | Vreman |
| 6,648,904 B2 | 11/2003 | Altshuler et al. |
| D484,601 S | 12/2003 | Griffiths et al. |
| D484,602 S | 12/2003 | Griffiths et al. |
| 6,660,027 B2 | 12/2003 | Gruszecki et al. |
| 6,667,883 B1 | 12/2003 | Solis et al. |
| 6,675,072 B1 | 1/2004 | Kerem |
| D486,870 S | 2/2004 | Mason |
| 6,695,823 B1 | 2/2004 | Lina et al. |
| 6,719,713 B2 | 4/2004 | Mason |
| 6,719,728 B2 | 4/2004 | Mason et al. |
| 6,736,787 B1 | 5/2004 | McEwen et al. |
| D492,411 S | 6/2004 | Bierman |
| 6,775,137 B2 | 8/2004 | Chu et al. |
| D496,108 S | 9/2004 | Machin et al. |
| 6,789,024 B1 | 9/2004 | Kochan, Jr. et al. |
| 6,802,823 B2 | 10/2004 | Mason |
| D499,846 S | 12/2004 | Cesko |
| 6,834,712 B2 | 12/2004 | Parish et al. |
| 6,846,295 B1 | 1/2005 | Ben-Nun |
| 6,848,498 B2 | 2/2005 | Seki et al. |
| 6,855,158 B2 * | 2/2005 | Stolpmann ................ 607/108 |
| 6,893,414 B2 | 5/2005 | Goble et al. |
| D506,553 S | 6/2005 | Tesluk |
| 6,935,409 B1 | 8/2005 | Parish, IV et al. |
| 6,936,019 B2 | 8/2005 | Mason |
| D510,140 S | 9/2005 | Brown |
| 6,945,988 B1 | 9/2005 | Jones |
| D510,626 S | 10/2005 | Krahner et al. |
| D515,218 S | 2/2006 | McGuire et al. |
| D523,147 S | 6/2006 | Tesluk |
| 7,066,949 B2 | 6/2006 | Gammons et al. |
| 7,081,128 B2 | 7/2006 | Hart et al. |
| D533,668 S | 12/2006 | Brown |
| D551,351 S | 9/2007 | Silva |
| D551,352 S | 9/2007 | Frangi |
| 7,306,568 B2 | 12/2007 | Diana |
| 7,354,411 B2 | 4/2008 | Perry et al. |
| D568,482 S | 5/2008 | Gramza et al. |
| D569,985 S | 5/2008 | Ganapathy et al. |
| 7,427,153 B1 | 9/2008 | Jacobs et al. |
| 7,429,252 B2 | 9/2008 | Sarangapani |
| 7,484,552 B2 | 2/2009 | Pfahnl |
| 7,492,252 B2 | 2/2009 | Maruyama |
| D595,620 S | 7/2009 | Kingsbury |
| D601,707 S | 10/2009 | Chouiller |
| D608,006 S | 1/2010 | Avitable et al. |
| D612,947 S | 3/2010 | Turtzo et al. |
| D613,870 S | 4/2010 | Shust |
| 7,717,869 B2 | 5/2010 | Eischen, Sr. |
| D618,358 S | 6/2010 | Avitable et al. |
| D619,267 S | 7/2010 | Beckwith et al. |
| D620,122 S | 7/2010 | Cotton |
| D625,018 S | 10/2010 | Smith et al. |
| D626,241 S | 10/2010 | Sagnip et al. |
| D626,242 S | 10/2010 | Sagnip et al. |
| D626,243 S | 10/2010 | Sagnip et al. |
| D626,245 S | 10/2010 | Sagnip et al. |
| D627,896 S | 11/2010 | Matsuo et al. |
| D628,300 S | 11/2010 | Caden |
| D630,759 S | 1/2011 | Matsuo et al. |
| 7,871,387 B2 | 1/2011 | Tordella et al. |
| D631,971 S | 2/2011 | Turtzo et al. |
| D633,657 S | 3/2011 | Oban |
| D634,437 S | 3/2011 | Gramza et al. |
| D634,851 S | 3/2011 | Chiang |
| D635,266 S | 3/2011 | Chiang |
| D635,267 S | 3/2011 | Chiang |
| 7,896,910 B2 | 3/2011 | Schirrmacher et al. |
| D636,497 S | 4/2011 | Giaccone |
| D638,950 S | 5/2011 | Janzon |
| D640,380 S | 6/2011 | Tweardy et al. |
| D640,381 S | 6/2011 | Tweardy et al. |
| D649,648 S | 11/2011 | Cavalieri et al. |
| 8,052,630 B2 | 11/2011 | Kloecker et al. |
| D655,420 S | 3/2012 | Bowles |
| D655,821 S | 3/2012 | Matsuo |
| D657,063 S | 4/2012 | Chiang |
| D660,438 S | 5/2012 | Kennedy et al. |
| D660,439 S | 5/2012 | Chen et al. |
| D663,850 S | 7/2012 | Joseph |
| D665,088 S | 8/2012 | Joseph |
| D665,470 S | 8/2012 | Galbraith |
| D666,258 S | 8/2012 | Campbell |
| D666,301 S | 8/2012 | Joseph |
| 8,449,483 B2 | 5/2013 | Eddy |
| 2001/0039439 A1 | 11/2001 | Elkins et al. |
| 2002/0116041 A1 | 8/2002 | Daoud |
| 2002/0143373 A1 | 10/2002 | Courtnage et al. |
| 2003/0050594 A1 | 3/2003 | Zamierowski |
| 2003/0083610 A1 | 5/2003 | McGrath et al. |
| 2003/0089486 A1 | 5/2003 | Parish et al. |
| 2003/0089487 A1 | 5/2003 | Parish, IV et al. |
| 2003/0127215 A1 | 7/2003 | Parish, IV et al. |
| 2003/0135252 A1 | 7/2003 | MacHold et al. |
| 2003/0163183 A1 | 8/2003 | Carson |
| 2003/0176822 A1 | 9/2003 | Morgenlander |
| 2004/0008483 A1 | 1/2004 | Cheon |
| 2004/0030281 A1 | 2/2004 | Goble et al. |
| 2004/0046108 A1 | 3/2004 | Spector |
| 2004/0054307 A1 | 3/2004 | Mason et al. |
| 2004/0068309 A1 | 4/2004 | Edelman |
| 2004/0068310 A1 | 4/2004 | Edelman |
| 2004/0099407 A1 | 5/2004 | Parish, IV et al. |
| 2004/0133135 A1 | 7/2004 | Diana |
| 2004/0186535 A1 | 9/2004 | Knowlton |
| 2004/0193218 A1 | 9/2004 | Butler |
| 2004/0210176 A1 | 10/2004 | Diana |
| 2004/0221604 A1 | 11/2004 | Ota et al. |
| 2004/0260231 A1 | 12/2004 | Goble et al. |
| 2005/0004636 A1 | 1/2005 | Noda et al. |
| 2005/0006061 A1 | 1/2005 | Quisenberry et al. |
| 2005/0033390 A1 | 2/2005 | McConnell |
| 2005/0039887 A1 | 2/2005 | Parish, IV et al. |
| 2005/0070828 A1 | 3/2005 | Hampson et al. |
| 2005/0070835 A1 | 3/2005 | Joshi |
| 2005/0133214 A1 | 6/2005 | Pfahnl |
| 2005/0143797 A1 | 6/2005 | Parish et al. |
| 2005/0177093 A1 | 8/2005 | Barry et al. |
| 2005/0182364 A1 | 8/2005 | Burchman |
| 2005/0256556 A1 | 11/2005 | Schirrmacher et al. |
| 2005/0274120 A1 | 12/2005 | Quisenberry et al. |
| 2005/0284615 A1 | 12/2005 | Parish et al. |

(56) References Cited

U.S. PATENT DOCUMENTS

| | | |
|---|---|---|
| 2006/0034053 A1 | 2/2006 | Parish et al. |
| 2006/0058714 A1 | 3/2006 | Rhoades |
| 2006/0116620 A1 | 6/2006 | Oyaski |
| 2006/0241549 A1 | 10/2006 | Sunnen |
| 2006/0276845 A1 | 12/2006 | George et al. |
| 2006/0282028 A1 | 12/2006 | Howard et al. |
| 2007/0032778 A1 | 2/2007 | Heaton et al. |
| 2007/0068651 A1 | 3/2007 | Gammons et al. |
| 2007/0112401 A1 | 5/2007 | Balachandran et al. |
| 2007/0118194 A1 | 5/2007 | Mason et al. |
| 2007/0129658 A1 | 6/2007 | Hampson et al. |
| 2007/0233209 A1 | 10/2007 | Whitehurst |
| 2007/0260162 A1 | 11/2007 | Meyer et al. |
| 2007/0282249 A1 | 12/2007 | Quisenberry |
| 2008/0058911 A1 | 3/2008 | Parish et al. |
| 2008/0064992 A1 | 3/2008 | Stewart et al. |
| 2008/0071330 A1 | 3/2008 | Quisenberry |
| 2008/0082029 A1 | 4/2008 | Diana |
| 2008/0103422 A1 | 5/2008 | Perry et al. |
| 2008/0132976 A1 | 6/2008 | Kane et al. |
| 2008/0249559 A1 | 10/2008 | Brown et al. |
| 2008/0319362 A1 | 12/2008 | Joseph |
| 2009/0109622 A1 | 4/2009 | Parish et al. |
| 2009/0149821 A1 | 6/2009 | Scherson et al. |
| 2009/0254160 A1 | 10/2009 | Shawver et al. |
| 2010/0010477 A1 | 1/2010 | Augustine et al. |
| 2010/0030306 A1 | 2/2010 | Edelman et al. |
| 2010/0081975 A1 | 4/2010 | Avitable et al. |
| 2010/0121230 A1 | 5/2010 | Vogel et al. |
| 2010/0137764 A1 | 6/2010 | Eddy |
| 2010/0145421 A1 | 6/2010 | Tomlinson et al. |
| 2010/0150991 A1 | 6/2010 | Bernstein |
| 2010/0249679 A1 | 9/2010 | Perry et al. |
| 2010/0249680 A1 | 9/2010 | Davis |
| 2011/0009785 A1 | 1/2011 | Meyer et al. |
| 2011/0034861 A1 | 2/2011 | Schaefer |
| 2011/0071447 A1 | 3/2011 | Liu et al. |
| 2011/0082401 A1 | 4/2011 | Iker et al. |
| 2011/0087142 A1 | 4/2011 | Ravikumar et al. |

FOREIGN PATENT DOCUMENTS

| | | |
|---|---|---|
| EP | 0 489 326 | 6/1992 |
| GB | 2373444 A | 9/2002 |
| SU | 689674 | 10/1979 |
| WO | WO-93/09727 | 5/1993 |
| WO | WO-00/40186 | 7/2000 |
| WO | WO-01/14012 A1 | 3/2001 |

OTHER PUBLICATIONS

J. Li, et al., "Enhanced germicidal effects of pulsed UV-LED irradiation on biofilms", Journal of Applied Microbiology, 2010, pp. 1-8.
Quisenberry, Tony, U.S. Appl. No. 13/359,210, filed Jan. 26, 2012.
U.S. Appl. No. 12/730,060, Parish et al.
U.S. Appl. No. 12/708,422, Balachandran et al.
Quisenberry, Tony, U.S. Appl. No. 29/424,860, filed Jun. 15, 2012.
Quisenberry, Tony, U.S. Appl. No. 13/456,410, filed Apr. 26, 2012.
U.S. Appl. No. 13/107,264, Quisenberry.
U.S. Appl. No. 12/364,434, Quisenberry.
U.S. Appl. No. 13/190,564, Quisenberry et al.
Copenheaver, Blaine R., "International Search Report" for PCT/US2012/035096 as mailed Aug. 7, 2012, 3 pages.
Quisenberry, Tony, U.S. Appl. No. 13/558,615, filed Jul. 26, 2012.
U.S. Appl. No. 29/397,856, Quisenberry.
U.S. Appl. No. 29/400,194, Quisenberry.
U.S. Appl. No. 29/400,202, Quisenberry.
U.S. Appl. No. 29/400,212, Quisenberry.
U.S. Appl. No. 29/402,115, Quisenberry.
U.S. Appl. No. 12/871,188, Parish et al.
Artikis, T., PCT International Preliminary Report on Patentability as mailed Jul. 29, 2005, (10 pgs.).
Tom Lee, T.Y. et al; "Compact Liquid Cooling System for Small, Moveable Electronic Equipment", IEEE Transactions on Components, Hybrids, and Manufacturing Technology, Oct. 15, 1992, No. 5, pp. 786-793.
Cyro/Temp Therapy Systems; Product News Catalogue; Jobst Institute, Inc., 6 pages.
Copenheaver, Blaine R., International Search Report for PCT/US2007/022148 as mailed Apr. 2, 2008, 2 pages.
Young, Lee W., "International Search Report" for PCT/US07/08807 as mailed Mar. 3, 2008, (3 pages).
U.S. Appl. No. 14/062,428, Quisenberry.
Copenheaver, Blaine R., "International Search Report" prepared for PCT/US2013/030475 as mailed May 23, 2013, 3 pages.

* cited by examiner

METHOD AND SYSTEM FOR THERMAL AND COMPRESSION THERAPY RELATIVE TO THE PREVENTION OF DEEP VEIN THROMBOSIS

CROSS-REFERENCE TO RELATED APPLICATIONS

The present application is a continuation-in-part of, and incorporates by reference for any purpose, the entire disclosure of U.S. patent application Ser. No. 11/733,709 filed Apr. 10, 2007 entitled "Method and system for thermal and compression therapy relative to the prevention of deep vein thrombosis," which claims the benefit of U.S. Provisional Application Nos. 60/791,132 filed Apr. 11, 2006 and 60/817,932 filed Jun. 30, 2006. The present application is a continuation-in-part of, and incorporates by reference for any purpose, the entire disclosure of U.S. patent application Ser. No. 10/894,369 filed Jul. 19, 2004 now abandoned entitled "Compression sequenced thermal therapy system," which claims the benefit of U.S. Provisional Application No. 60/488,709 filed Jul. 18, 2003, No. 60/550,658 filed Mar. 5, 2004, and 60/588,453 filed Jul. 6, 2004.

BACKGROUND OF THE INVENTION

1. Technical Field

The present invention relates to medical therapy systems in general, including therapeutic cooling, heating, and compression systems used in association therewith, and more particularly, but not by way of limitation, to a programmable, thermal therapy and external pneumatic compression for the prevention of deep vein thrombosis.

2. Description of the Related Art

Considerable medical attention has been given to the serious medical issue of Deep Vein Thrombosis ("DVT"). One approach to the prevention of DVT has been External Pneumatic Compressions ("EPC"). EPC has been shown to be helpful as a prophylaxis for DVT, although refinements over existing systems are still in need. For example, multiple articles have been written addressing this issue, including a compilation of recommendations for preventing DVT (Heit J A: Current Recommendations for Prevention of Deep Venous Thrombosis. In: *Handbook of Venous Disorders*. Gloviczki P, Yao J S, eds. Cambridge, The University Press, 1996). Engineering studies are presented which also address EPC as a preventative for DVT (Kamm R D: Bioengineering Studies of Periodic External Compression as Prophylaxis Against Deep Vein Thrombosis—Part 1: Numerical Studies. *J Biomech Engineering* 104(1): 87-95, 1982). Such efforts are meritorious for patient health due to possible Pulmonary Embolism ("PE") resulting from DVT (National Institutes of Health Consensus Development Conference Statement: Prevention of Venous Thrombosis and Pulmonary Embolism. *JAMA* 6(2) 744-749, 1986). Additionally, studies have been performed relative to DVT and orthopedic surgery ("OS") (Westrich G H, Sculco T P: Prophylaxis Against Deep Vein Thrombosis After Total Knee Arthroplasty. *J Bone Joint Surg* 78-A(6): 826-834, 1996).

Relative to OS, physicians have long recognized the need to provide warmth and cooling directly to patients as part of OS therapy. Better recoveries have been reported, for example, using cold therapy for orthopedic patients. The benefits of warming patients undergoing surgery has also been demonstrated. It may also be desirable to cool portions of a patient's anatomy in certain circumstances. Yet another advantageous therapy is the application of heat then cold to certain injured areas. See, for example, U.S. Pat. No. 5,989,285 (the '285 Patent) assigned to Thermotek, Inc. and incorporated herein by reference.

Several devices have been developed that deliver temperature-controlled fluids through pads or convective thermal blankets to achieve the above thermal purpose. Typically these devices have a heating or a cooling element, a source for the fluid, a pump for forcing the fluid through the pad or blanket, and a thermal interface between the patient and the temperature-controlled fluid. U.S. Pat. No. 4,884,304 to Elkins is directed to a mattress-cover device that contains liquid flow channels that provide the selective heating or cooling by conduction.

Devices have also been developed for providing heat to a person in bed. Electric blankets containing electric heating elements have been used for years to warm a person in bed. Cooling blankets, such as the blanket disclosed in U.S. Pat. No. 4,660,388 to Greene, have also been proposed. Greene discloses a cooling cover having an inflatable pad with plenum chambers at opposite ends thereof. Cool gas is generated in a separate unit and directed to the pad and out a number of apertures on the underside of the pad and against the body of the person using the cover.

A disposable heating or cooling blanket that has three layers of flexible sheeting is disclosed in U.S. Pat. No. 5,125,238 to Ragan, et al. Two of the layers form an gas chamber and the third includes a comfortable layer for contact with the patient. Conditioned gas is directed toward the covered person through a multiplicity of orifices in the bottom layers of the blanket.

The temperature-controlled blanket and bedding assembly disclosed in the '285 Patent includes a temperature-controlled blanket and temperature-controlled bedding system that provide both recirculating temperature-controlled fluid and temperature-controlled gas to enhance performance for convectively heating or cooling a patient. Counter-flow or co-flow heat-exchanging principles between the temperature-controlled liquid and the temperature-controlled gas achieve temperature uniformity across different sections of the blanket and the bedding system. Drapes and the temperature-controlled bedding system provide a temperature-controlled envelope around a person using the bedding system. In one embodiment of the bedding system, an gas portion of the bedding system is provided that supplies a fluid portion of the overall bedding system. In another embodiment of the bedding system, the fluid portion of the bedding system is provided for use with a patient bed that supplies the gas portion of the overall bedding system.

U.S. Pat. No. 5,097,829 to Quisenberry describes an improved temperature-controlled fluid-circulating system for automatically cooling a temperature-controlled fluid in a thermal blanket with a thermoelectric-cooling device having a cold side and a hot side when powered by electricity. The temperature-controlled fluid is cooled by a cold side of the cooling device and is pumped through, to, and from the blanket through first and second conduits.

BRIEF SUMMARY OF THE INVENTION

The present invention relates to thermal therapy and compression therapy for use in heating and/or cooling a patient and providing compression. In one aspect of the invention, a DVT therapy system includes at least a control unit, one or more thermal-treatment blankets, one or more compressive-therapy treatment devices, and a plurality of connector tubes. The control unit may be adapted to heat and/or cool a heat-transfer liquid within about 37-105° F. and to provide compressed gas at a pressure of greater than around 25 mm Hg above ambient atmospheric pressure, but the ranges may also include lower and/or higher temperatures and pressures. The one or more thermal-treatment blankets may be adapted for receipt of the heat-transfer liquid from the control unit and for return of the heat-transfer liquid back to the control unit via the connector tubes. The one or more compressive-therapy treatment devices may be adapted to utilize the compressed gas from the control unit via connector tubes.

In another aspect, a DVT method includes providing a control unit adapted to heat and/or cool a heat-transfer liquid to a temperature within the range of about 37-105° F. and adapted to provide compressed gas at a pressure of at least 25 mmHg above ambient atmospheric pressure, providing a thermal treatment blanket adapted for receipt of the heat-transfer liquid from the control unit and for sending the heat-transfer liquid back to the control unit, and applying a hot or cold treatment to an individual. The method may also include providing a compressive-therapy treatment device utilizing the compressed gas from the control unit and applying a compressive treatment to an individual.

In another aspect, a DVT therapy method may include a method of providing sequenced thermal therapy, sequenced compression therapy, and/or DVT therapy to parts of a body. The method may include providing a control unit adapted to thermally control, such as heating and/or cooling, a heat transfer fluid and adapted to provide compressed gas, providing a thermal blanket adapted to receive the heat transfer fluid from the control unit and return the heat transfer fluid to the control unit via one or more connector tubes, and also adapted to receive the compressed gas from the control unit via one or more connector tubes, providing one or more DVT compression devices adapted to utilize the compressed gas from the control unit via one or more connector tubes, and applying the thermal treatment, the compression treatment, and the DVT treatment to the individual in multiple modalities regulated by the control unit. The multiple modalities may include sequencing and/or alternating between the treatments.

In another aspect, a DVT therapy system may include a system for providing multiple modalities of thermal therapy, compression therapy, and/or DVT therapy, and may include sequentially applying the therapies. The system may include a control unit adapted to heat and/or cool a heat-transfer liquid and to provide compression; a thermal-treatment blanket adapted to receive the heat-transfer liquid from the control unit and to send the heat-transfer liquid back to the control unit; a compressive-therapy treatment device adapted to utilize the compressed gas from the control unit; and/or a DVT treatment device adapted to utilize the compressed gas from the control.

BRIEF DESCRIPTION OF THE DRAWINGS

A more complete understanding of the method and apparatus of the present invention may be obtained by reference to the following Detailed Description when taken in conjunction with the accompanying Drawings wherein.

DETAILED DESCRIPTION OF ILLUSTRATIVE EMBODIMENTS OF THE INVENTION

Applicants have discovered that the use of both thermal therapy and compression therapy for the prevention of DVT may be advantageous. As referenced above, numerous articles have been written on the problems associated with DVT and the utilization of thermal therapy is already well known. Consistent therewith, methods of and systems for providing pressurized and thermally controlled fluids for use with patients in need of such therapy are disclosed. A versatile control unit is adapted for providing one of a plurality of treatment modalities. As will be described below, one modality provides a thermally controlled liquid adapted to flow through a treatment pad or blanket for thermal therapy. A second modality provides compressed gas to a treatment pad or blanket to cause a degree of compression relative to a patient. A third modality provides compressed gas to DVT therapy modules so that the prevention of DVT can be afforded. In various embodiments, each of the above modalities may be provided in a single treatment regimen.

As will be described in more detail below, a control unit is shown that is adapted to provide thermally controlled fluid and compressed gas for multiple therapeutic modalities. The control unit for providing these selective features may be enclosed within a single chassis design capable of providing the described modalities. This selective versatility provides financial and manufacturing incentives in that the simple design selectively can provide an industrial, medical, or electro-optic version that produces only thermally controlled liquid, such as co-liquid for cooling industrial equipment, in a configuration adaptable for other applications. In one embodiment, the size of the reservoir has been reduced relative to a number of earlier models of thermoelectric cooler (TEC) systems such that only around 175 Watts may be needed compared to 205 Watts for typical earlier systems. As such, the control unit may be configurable with TEC assemblies maximizing efficiency. With regard to a medical modality, thermal therapy may be afforded to a patient to reduce swelling and edema while, in conjunction with the DVT prophylaxis, preventing blood from pooling in lower body extremities. This is particularly important after surgery when anesthesia has been involved. It is well known that anesthetics often tend to reduce the wall strength of veins and, if not otherwise treated, appropriate venous pumping may not be afforded allowing for blood pooling in clots.

Figure 1:
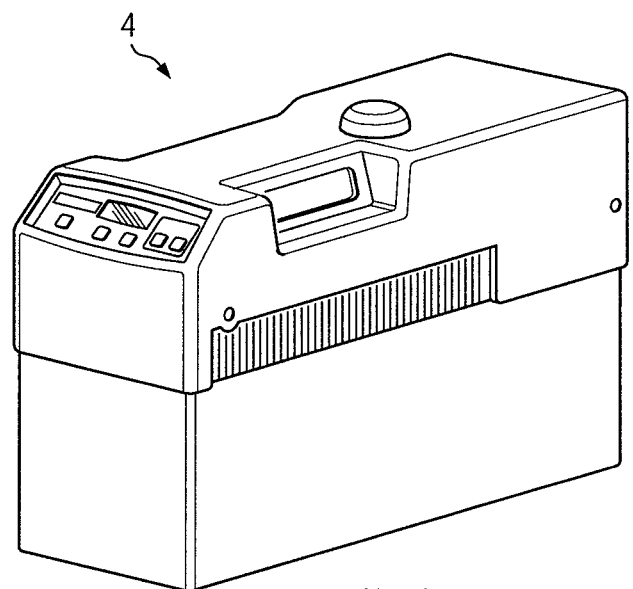
FIG. 1 is a perspective view of a thermal and compression control unit for thermal and compression therapy relative to the prevention of DVT.

Referring now to FIG. 1, there is shown a thermal and compression-control unit 4 for thermal and compression therapy. The control unit 4 may be adapted to be coupled to thermal and compression elements to be applied to a patient as described below. In this particular view, the control unit 4 is shown in perspective to illustrate the assembly of one embodiment of a control unit for pumping gas and liquid through tubes to be described below for a patient to be treated therewith.

Referring still to FIG. 1, a lower dark portion thereof includes a filter that is removable from around a grate as illustrated below. In one embodiment, the filter provides an gas-filtering substance such as woven netting that may be attached by VELCRO fasteners or the like outwardly of a perforated metal grate to allow for the low-pressure drawing of gas therethrough to allow cooling of components placed inwardly therein prior to the upward draw of the gas through fans disposed thereabove and the forcing of the gas across one or more heat transfer assemblies (HTA).

Figure 2:
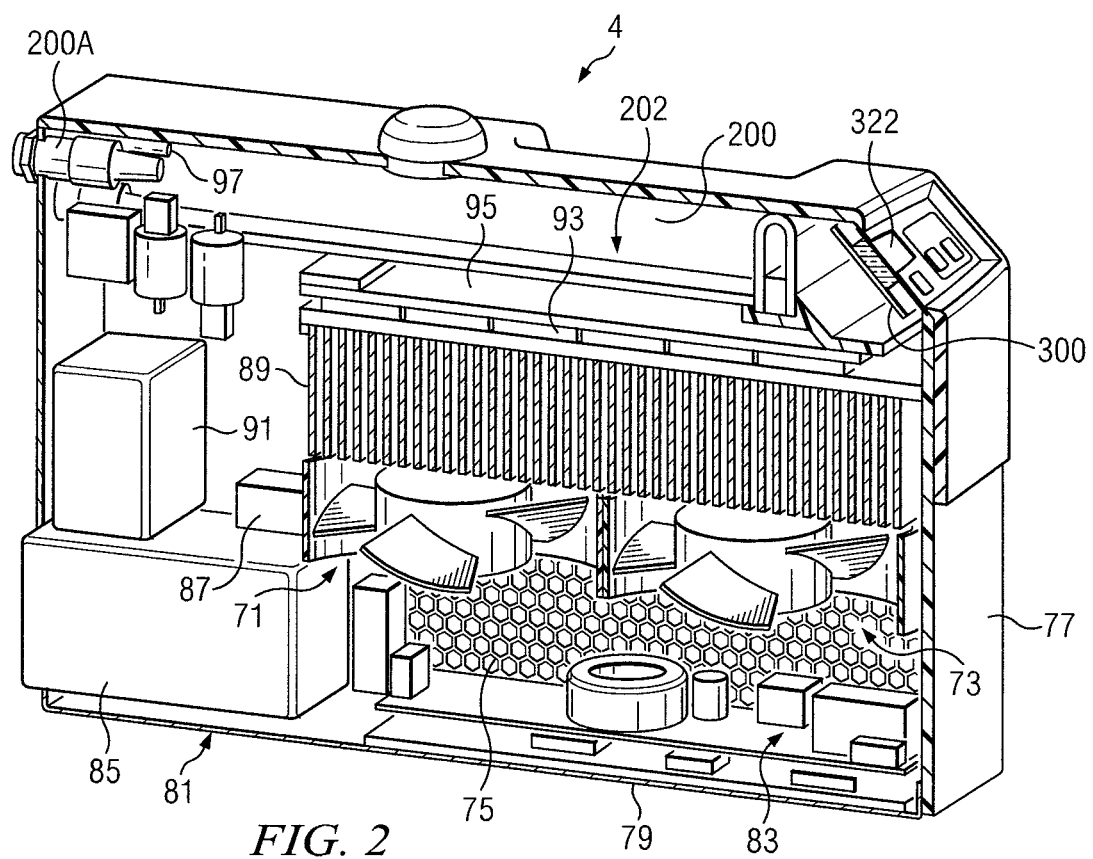
FIG. 2 is a cut-away, perspective view of the control of FIG. 1 illustrating various elements thereof.

Referring now to FIG. 2, an HTA 202 is shown disposed beneath a fluid reservoir 200. The reservoir 200 is adapted for storage of liquid that may be pumped outwardly through a fluid connector 200A disposed rearwardly of the reservoir 200. Fluid connector 200A is adapted for being coupled to one or more pads or blankets via connector tubes as described below.

Still referring to FIG. 2, there is shown an internal portion of the control unit 4 referenced above illustrating one embodiment of the assembly therein. Within the assembly of the unit 4, a of fans 71 and 73 are shown disposed above a grate 75. Grate 75 contains therearound the filter portion 77 that may be secured thereto by hook and loop (e.g., VELCRO). A lower portion of the grate 73 may be connected to a bottom portion 79 of a chassis 81 in a manner to provide support for electronic components 83 mounted thereon for providing an adequate supply of power to and control of the HTA 202 and other elements within the control unit 4. In some embodiments, a dual-fan arrangement may be utilized. As shown, fans 71 and 73 may be positioned to push and/or pull gas from the grate 75 disposed peripherally about the electronic components so that the gas flow is both quiet and at a rate allowing initial electronic cooling and then being available to be pushed into the top section of the control unit 4 where most heat dissipation is needed.

Referring still to FIG. 2, a power supply 85 is disposed in a lower portion of a chassis 81 and beneath an gas switch 87 disposed beneath a heat sink 89 and adjacent to a fluid pump 91. Various embodiments, the power supply 85 may be a 500 Watt power supply. In some embodiments, additional power supplies may also be utilized to power various components. For example, in addition to a 500 Watt power supply, a 65 Watt power supply may be utilized for components requiring less power. In some embodiments, the power supplies are adapted to receive a plurality of inputs so the control unit 4 can be utilized in a plurality of countries without requiring substantial reconfiguration.

Still referring to FIG. 2, the fluid pump 91 is shown disposed in a position for collecting fluid from a reservoir 200 that has been thermally controlled by the HTA 202 for passage through the fluid connector 200A. TECs 93 are shown disposed between the heat sink 89 and a thermal transfer plate 95 in a manner to provide the requisite thermal control of the fluid within the reservoir 200. An gas connector 97 is shown disposed adjacent to the fluid connector 200A to provide the requisite dissipation of gas for use in conjunction with a blanket, for example, to apply pressure in a bladder to force thermal fluid flowing from the fluid connector 200A to be in close contact with the patient as will be described below.

Figure 3:
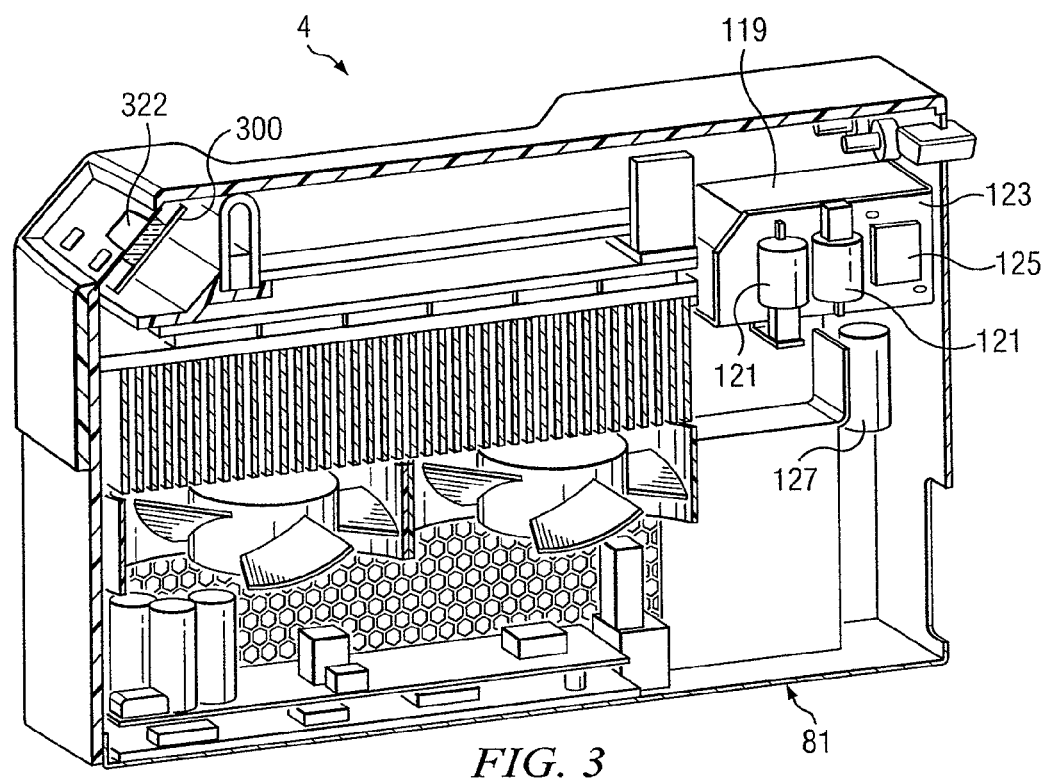
FIG. 3 is a cut-away, perspective view of the control unit of FIG. 1 taken from the opposite side of that in FIG. 2.

Referring now to FIG. 3, there is shown a cutaway perspective view of the control unit 4 taken from an opposite side thereof and illustrating various other aspects therein. In conjunction with the DVT therapy operation, a DVT gas pump 119 is shown disposed adjacent to a pair of DVT solenoids 121 mounted on a DVT gas bracket 123 adjacent a DVT gas switch 125. A solenoid 127 is likewise disposed relative thereto, while in various embodiments, more or less solenoids and/or gas switches may be disposed therein as needed.

Figure 4:
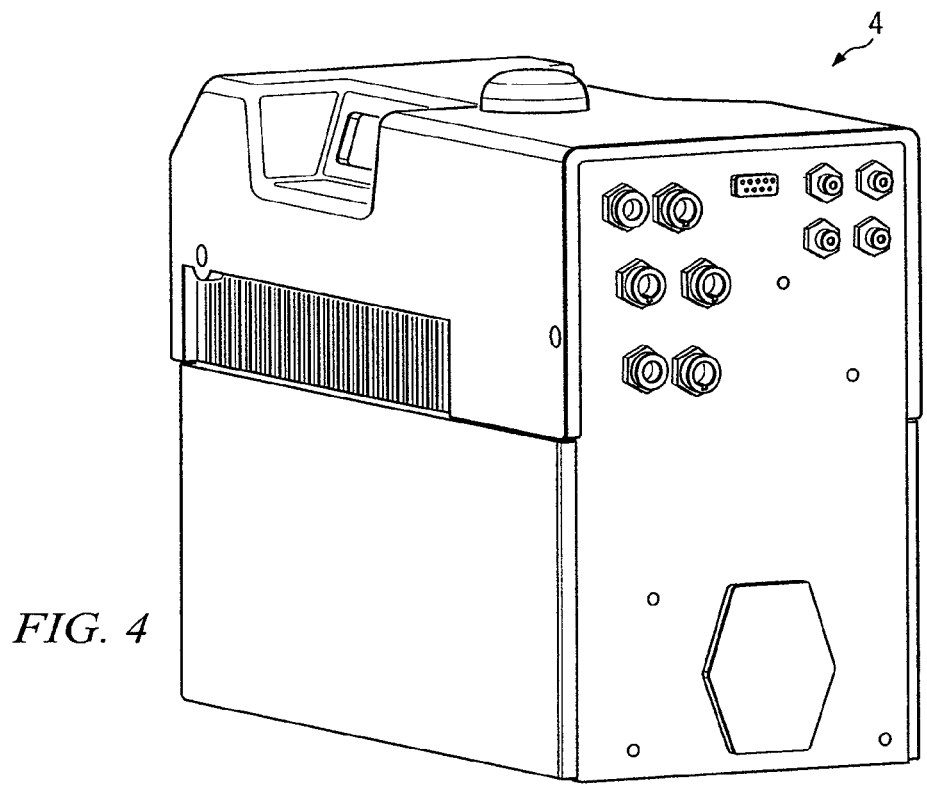
FIG. 4 is a rearwardly oriented, perspective view of the control unit of FIG. 1.

Referring now to FIG. 4, there is shown a rearward-oriented perspective view of the control unit 4 illustrating the connectors and couplings on the rear panel of the control unit 4 as provided for the functionality described herein. In this particular view, it may be seen that a plurality of gas connectors and fluid connectors may be utilized to provide thermally conditioned heat-transfer fluid to a plurality of thermal therapy devices and to provide pressurized gas to a plurality of compression therapy devices and DVT compression devices. In some embodiments, the fluid connectors are provided in pairs to facilitate circulation of fluid in a closed loop in an outward bound and an inward bound flow of fluid to and from the fluid reservoir for thermal control. In some embodiments, a single compression therapy device may be coupled to a plurality of gas connectors and the control unit may be programmed accordingly to provide compressed gas in a sequenced manner to a plurality of bladders in the compression therapy device. For example, a first bladder may be inflated, followed by the inflation of a second bladder, which is then followed by the inflation of a third bladder, and so on. The first bladder may be deflated before or after the second bladder is inflated, or the first bladder may remain inflated until all the bladders are inflated. In some embodiments, the DVT connectors are provided in pairs, although a single DVT connector may be used for each DVT pad or a plurality of connectors may be used. The DVT pads are pressurized in accordance with the medical modality described herein and the parameters are set by the programming within the control boards of the control unit 4. Also shown in the figure is an RS232 connector for data communication with the control unit 4. In other embodiments, other connections may be utilized such as, for example, a USB connection or a wireless connection.

Figure 5:
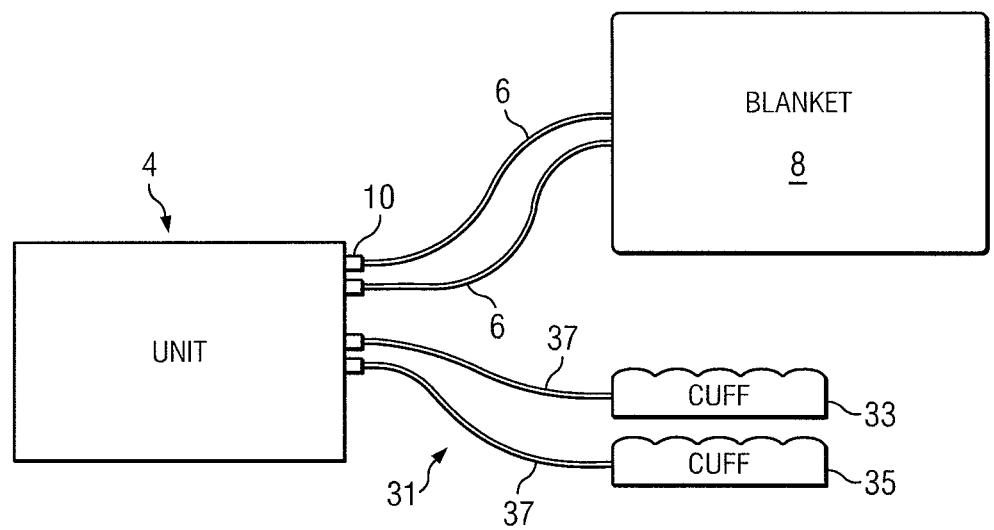
FIG. 5 is a diagrammatic schematic of a DVT-therapy system illustrating integration of thermal and compression elements.

Referring now to FIG. 5, there is shown a thermal compression-control system for thermal compression therapy wherein the control unit 4 is coupled to a thermal blanket 8 by connector tubes 6 coupled to the control unit 4 through a connector 10. The DVT prevention aspect is provided through a cuff system 31 comprising cuffs 33 and 35 that allow placement on the feet or other select regions of a patient for the DVT treatment thereof The cuffs 33 and 35 are coupled to the control unit 4 through connector tubes 37. Relative to the DVT pulsing, various embodiments of the present invention provide for a user to specify the control unit 4 to generate either a broad pulse or a narrow pulse, wherein a broad pulse may include a longer ramp-up time and a narrow pulse may include a shorter ramp-up time. With either pulse width, an amount of compressed gas is provided to a first DVT cuff 33 for a user-specified amount of time and at a user-specified pressure followed by an amount of compressed gas being provided to a second DVT cuff 35. The DVT pulses may be provided in rapid succession or a user-specified period of time may elapse between pulses. In some embodiments, a narrow pulse may be generated by opening a solenoid on compressed gas which may provide an increased intensity of the pulse. In some embodiments, a plurality of solenoids may be utilized which may permit choosing between the right or left routing of the compressed gas.

Still referring to FIG. 5, it may be seen that the connector tubes 37 are coupled to the control unit 4 wherein each may provide a pressurized gas in accordance with a pre-programmed application or user-specified parameters to maximize the effectiveness of the DVT prophylaxis. One activation technique is a high pressure low ramp-up sequence wherein the select pressure for DVT prevention is provided without a high pulse rate. A high pulse-rate time may be advantageous in such a DVT prevention system to modify the conventional pulse rate and thereby reduce cell damage. In this manner, the control boards of the control unit 4 provide a select pressurization in utilization with the solenoids shown mounted within the DVT system to carefully control the pulse ramp time in accordance with maximum medical treatment of the patient pursuant to medical concerns for such treatment.

In various embodiments, different sequencing patterns, times, and pressures may be utilized depending on the type of treatment desired. Various embodiments allow a plurality of parameters to be specified by a user, such as, for example, the inflated pressure, the deflated pressure, the rate of inflation, the inflation-hold time, and the cycle time. For example, in one treatment modality, the control unit may provide compressed gas to inflate a DVT compression device for 3-20 seconds when the DVT compression device is disposed on a calf. The time period of the pulse may be more or less depending on the part of the body being treated. For example, a pulse width of around 0.3 seconds may be desirable for a foot. Similarly, the inflation times may vary depending on whether DVT compression devices located on both right and left extremities are being inflated simultaneously or whether the inflation is being alternated between the devices. For example, an inflation period of 18 seconds may be desirable for simultaneous inflation whereas an inflation period of 8 seconds may be desirable when the inflation is being alternated. Similarly, when DVT compression devices are disposed around a patient's right and left feet, in some situations it may be desirable to have a wide pulse width on the order of 9 seconds whereas in other situations it may be desirable to have a narrow pulse width on the order of 0.3 seconds. In addition, it may be desirable to vary the cycle times in between DVT pulses. For example, in some embodiments, a cycle time of 20 seconds in between DVT pulses may be desirable. Similarly, in some embodiments, it may be desirable to completely deflate the DVT compression devices in between inflations while in other embodiments, it may be desirable to keep the DVT compression devices partially inflated. As can be seen from the above examples, it would be desirable to have a programmable control unit that can be adapted to provide DVT compression at user-specified parameters.

Figure 6:
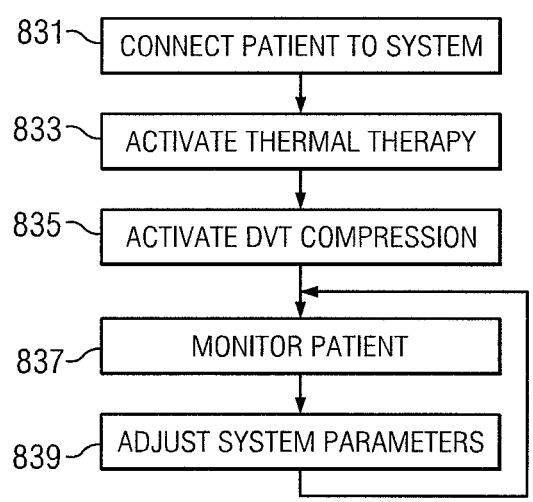
FIG. 6 is a flow diagram illustrating a thermal therapy and DVT compression process.

Referring now to FIG. 6, there is shown a flow diagram illustrating an embodiment wherein the patient is initially connected to the system of control unit 4 in step 831. Next, thermal therapy is activated at step 833. In some embodiments, activating thermal therapy may include providing compressed gas to the thermal therapy device. Compressing the thermal therapy device may increase the thermal transfer fivefold or more. At step 835, the DVT compression is activated. When compression is provided in conjunction with thermal therapy, it is often desirable to stop the compression during the time period that the DVT compression is activated on the same extremity. For example, when a right knee is receiving thermal and compression therapy and the right and left feet of a patient are receiving DVT compression, it may be beneficial to stop the compression on the right knee every time the right foot received DVT compression. The condition of the patient is monitored in step 837 and the control parameters are adjusted in step 839 for further monitoring of the patient. Adjustments in step 839 follow monitoring the patient in step 837 as long as the system is in operation. It is also contemplated that the order of the above mentioned steps may be varied and/or some or all of the steps may be skipped or repeated to maximize efficiency.

Figure 7:
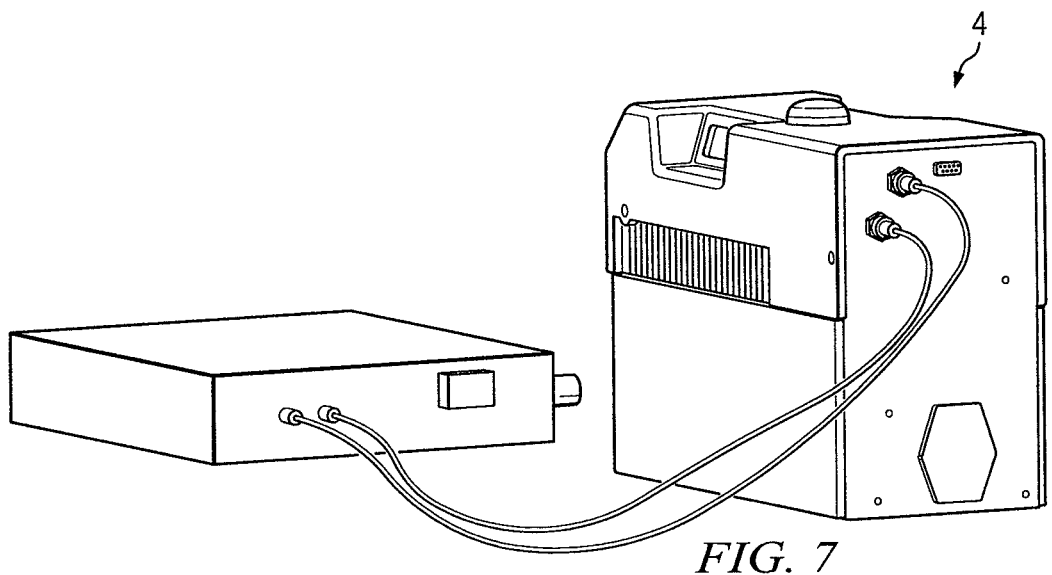
FIGS. 7-10 illustrate various aspects of various embodiments of the present invention.
Figure 8:
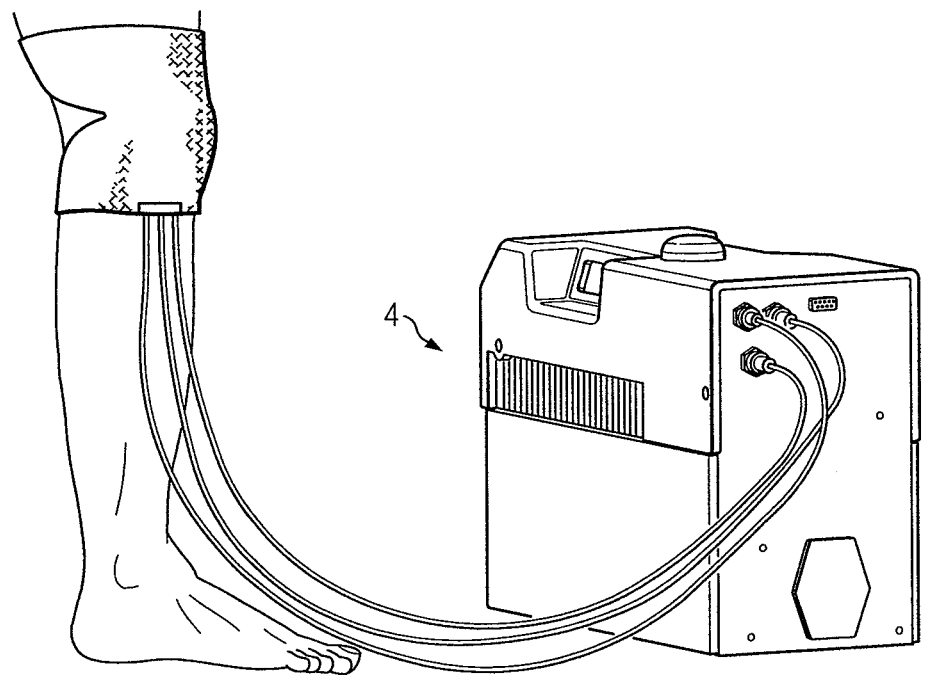

Referring now to FIGS. 7-10 together, various aspects of a plurality of embodiments are shown. In FIG. 7, an industrial example is illustrated wherein a cooling umbilical is provided from control unit 4, which cooling umbilical may be utilized to cool electronic equipment as therein illustrated. Likewise in FIG. 8, the control unit 4 is shown to be connected to a therapy device with three tubes. In some embodiments, two of the tubes may be delivering and returning a heat transfer fluid to and from the control unit 4 and the third tube may be delivering compressed gas for compression of the therapy device. In other embodiments, all three of the tubes may be delivering compressed gas in a sequenced manner to the therapy device. For example, a first bladder may be inflated by compressed gas delivered via a first tube followed by the inflation of a second bladder inflated by compressed gas delivered via a second tube. A third bladder may then be inflated by compressed gas delivered via a third tube. Additional tubes and/or bladders may also be utilized. The first bladder may be deflated before or after the second bladder is inflated, or the first bladder may remain inflated until all the bladders are inflated. The bladders may be inflated in a sequence extending outwardly from the heart, may be inflated in a sequence inwardly towards the heart, or may be inflated in any user-specified pattern depending on the results desired. The embodiment shown is a wrap for use around a patient's knee, but similar wraps may also be used around any body part of a patient needing compression and/or thermal therapy, such as, for example, a user's feet, calves, ankles, arms, or other areas.

Figure 9:
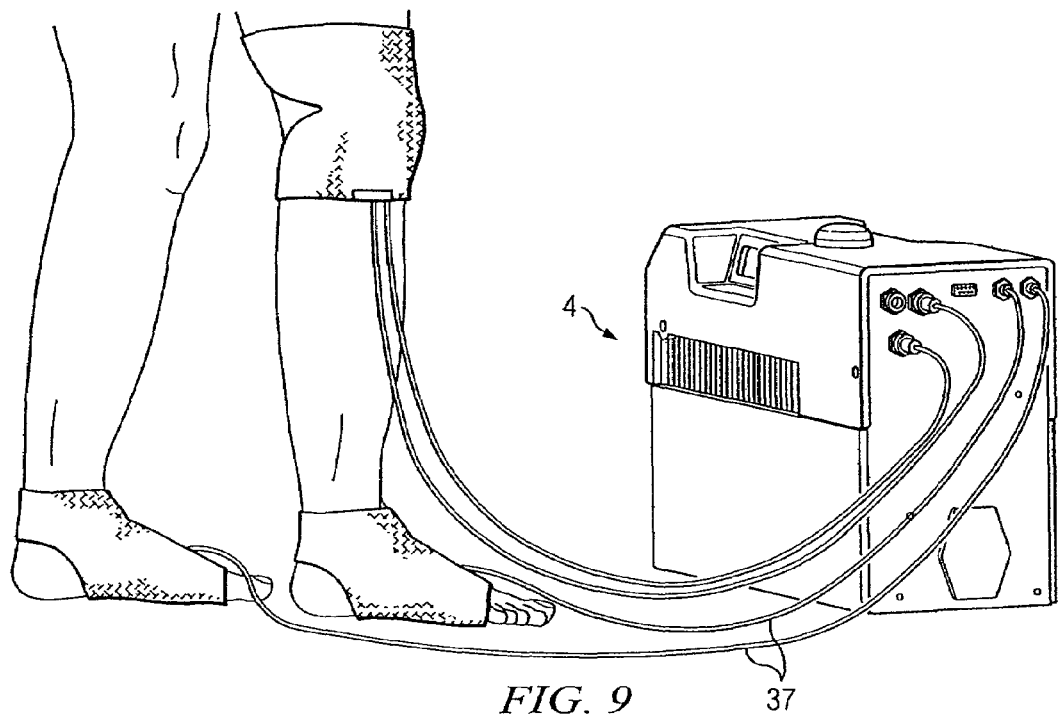
Figure 10:
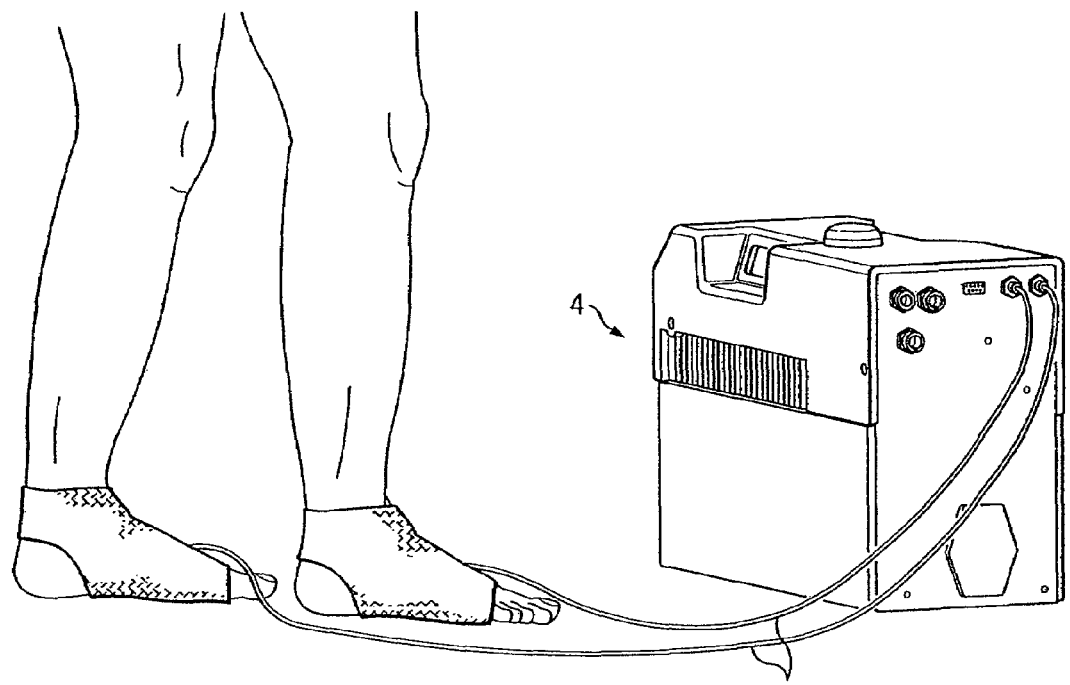

Referring now to FIG. 9, a control unit 4 is shown connected to a compression/thermal therapy device and two DVT compression devices. As can be seen, DVT compression is being provided to a patient's right and left feet. Often times, pulses of compressed gas are alternated between the DVT compression devices on the right and left feet. At the same time, as can be seen, thermal and/or compression therapy may be provided to a knee of a patient. When a pulse of compressed gas is provided to a DVT compression device disposed on the same extremity as a thermal/compression therapy device, it is often desirable to deflate the thermal/compression therapy device. In that way, the thermal/compression therapy device will not impede any fluidic movement caused by the DVT compression device. In FIG. 10, only DVT is being utilized from the control unit 4 as no thermal therapy umbilicals are therein utilized. As shown in FIGS. 9 and 10, the feet/ankle areas are covered, but other body parts may be covered, such as, for example, calves, knees, arms, or other areas for purposes of applying pressure thereagainst Referring now to FIG. 11A, there is shown a DVT flat foot blanket layout 1100 of the type that may be used as a DVT compression device for a foot and/or ankle region. Because of the generic shape of the flat foot blanket layout 1100, a foot wrap based on the layout 1100 may be used on either a left or right foot. It may be understood that a variety of blanket layouts may be utilized for the foot during DVT treatment. The illustrations as depicted in FIGS. 7-11 represent exemplary embodiments, but a plurality of other embodiments are also contemplated.

Figure 11A:
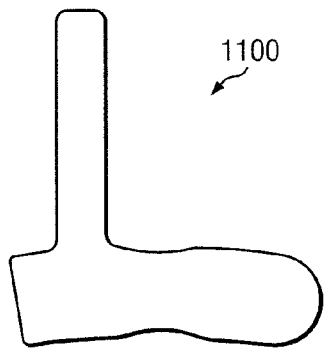
FIGS. 11A-11G illustrate a DVT foot wrap.
Figure 11B:
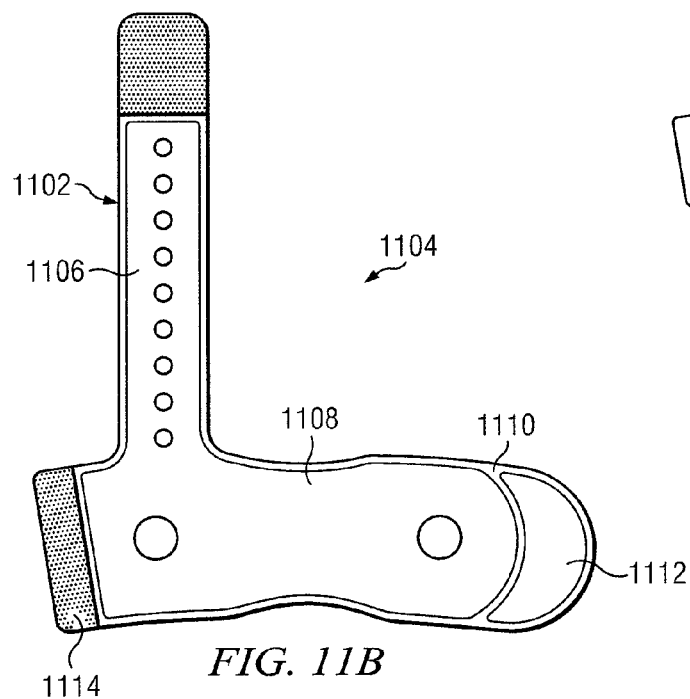
Figure 11C:
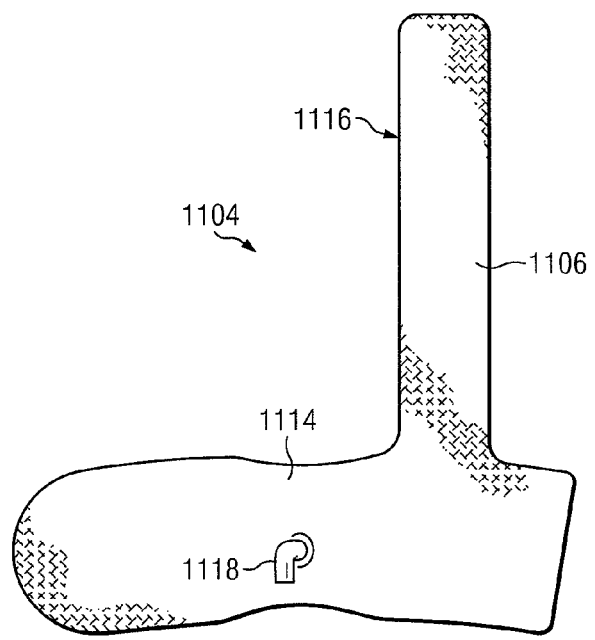

Referring now to FIGS. 11B-11C, there is shown a contoured foot wrap 1104. The foot wrap 1104 is formed from a first sheet of biocompatible material 1102 and a second sheet of biocompatible material 1116 that are sealed together at sealed edge 1110. The first sheet of biocompatible material 1102 and the second sheet of biocompatible material 1116 include the front and back of the foot wrap 1104, respectively. The foot wrap 1104 includes an upper gas-tight inflatable portion 1106 and a lower gas-tight inflatable portion 1108. The lower gas-tight inflatable portion 1108 also includes flaps 1112 and 1114. In various embodiments, flap 1114 and the upper gas-tight inflatable portion 1106 include a hook-and-loop fastener hook sealed or sewn onto their front sides and the back 1116 is Velcro® compatible to receive the hooks. An inlet 1118 is located on the back of the foot wrap 1104 on the lower gas-tight inflatable portion 1108 to facilitate the intake and exhaust of gas.

Figure 11D:
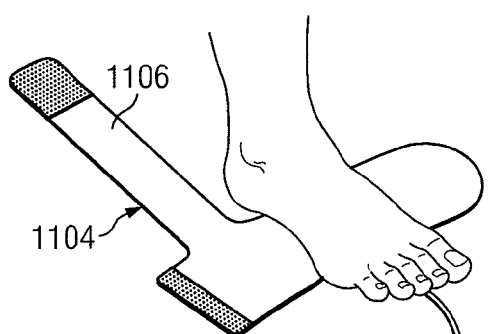
Figure 11E:
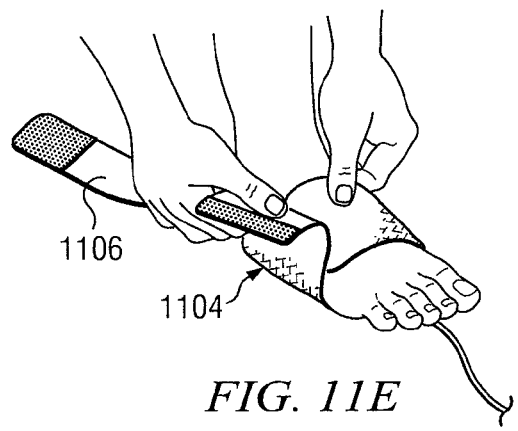
Figure 11F:
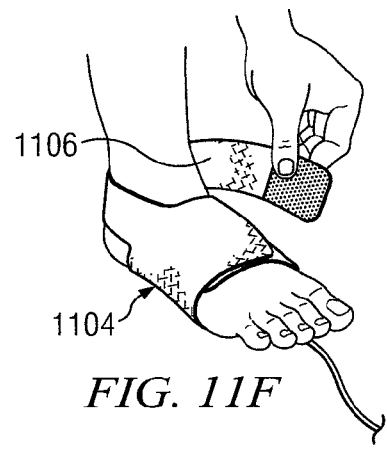
Figure 11G:
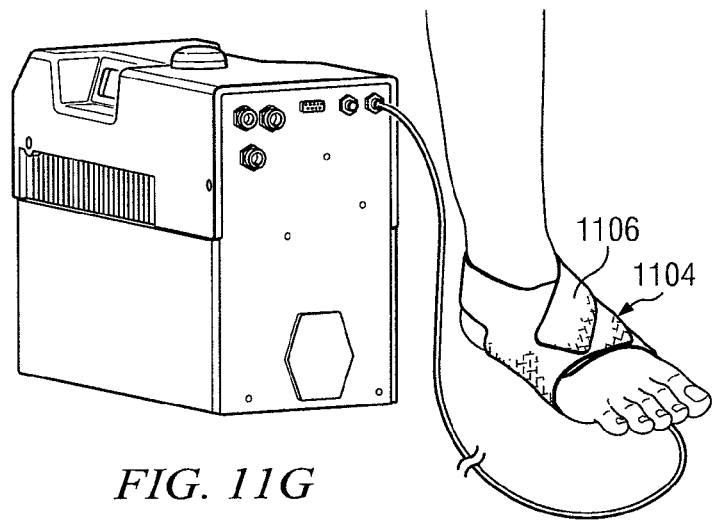

Referring now to FIGS. 11D-11G, the operation of the foot wrap 1104 is described. With reference to FIG. 11D-11E, a foot is placed into the foot wrap 1104 with the foot engaging the front side 1102 of the foot wrap 1104. With reference to FIGS. 11E-11F, the flaps are pulled tight and the foot wrap 1104 is secured. The contoured foot wrap 1104 may be now be connected to the control unit 4 via a DVT connector 37 connected to inlet 1118 for DVT therapy, as depicted in FIG. 11G.

Figure 18A:
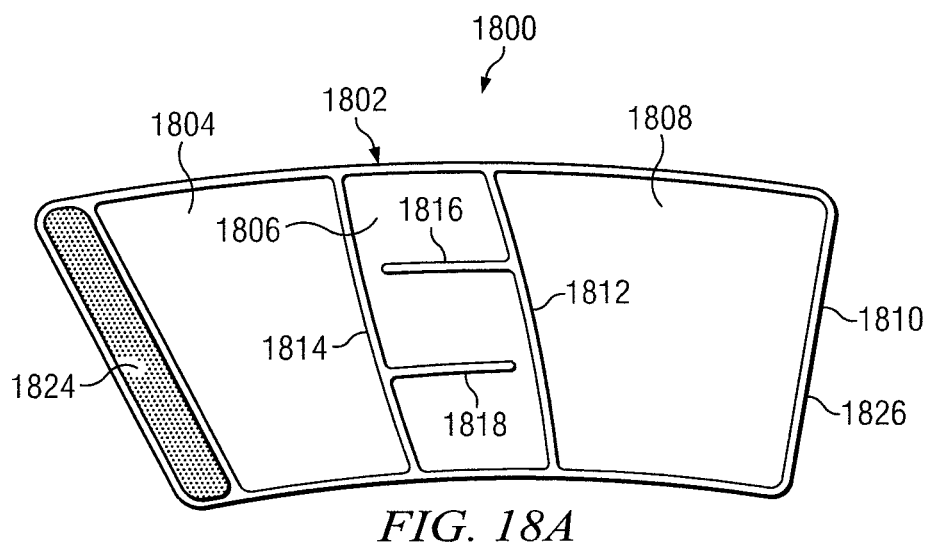
FIGS. 18A-18D illustrate a DVT calf wrap.
Figure 18B:
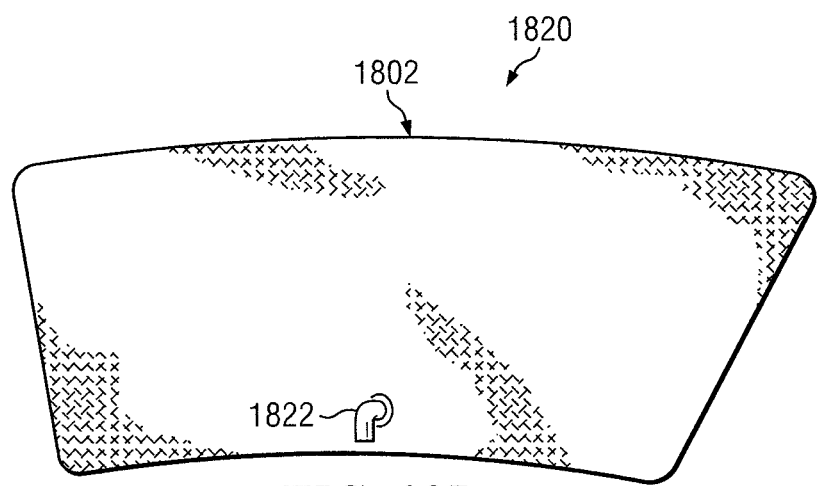

Referring now to FIGS. 18A-18B, there is shown a trapezoidal DVT calf blanket 1802 of the type that may be used for DVT therapy. As with the flat foot blanket layout, a variety of blanket layouts may be used for the calf during DVT treatment. A calf wrap 1802 is formed of two sheets of biocompatible material 1800 and 1820, including the front and back of the calf wrap 1802, respectively. The front 1800 and back 1820 are sealed or sewn together at a sealed edge 1810. Additionally, the calf wrap is divided into three chambers (1804, 1806, and 1808) by welds 1812 and 1814. The middle chamber 1806 is characterized by two additional welds 1816 and 1818. Weld 1816 extends from weld 1812 and weld 1818 extends from weld 1814, creating an 'S' shaped chamber. The three-chamber structure as described herein permits a compression gradient across the three chambers. In various embodiments, all welding may be accomplished by radio frequency (RF) welding. The front side 1800 also includes flaps 1824 and 1810. In various embodiments, flap 1824 may have sealed or sewn thereon a Velcro® hook and back side 1820 may be Velcro® compatible to receive the hook. An inlet 1822 is located on the back of the calf wrap 1802 to facilitate the intake and exhaust of gas.

Figure 18C:
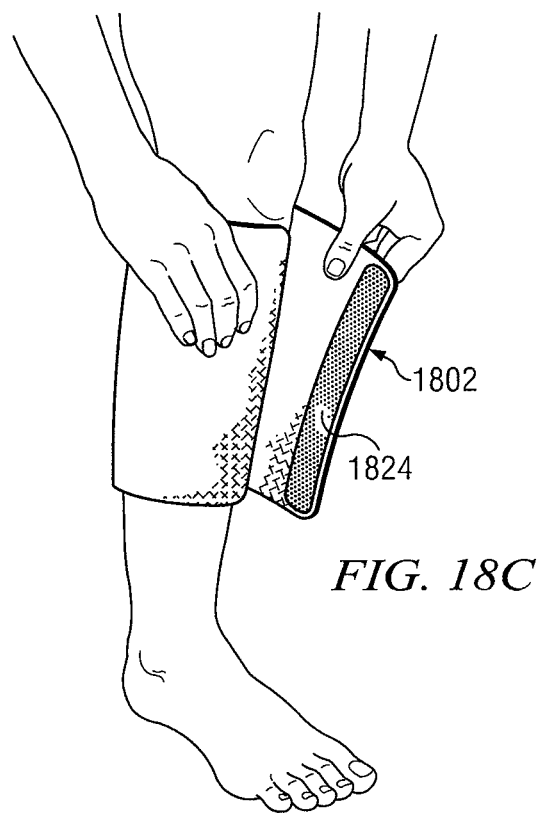
Figure 18D:
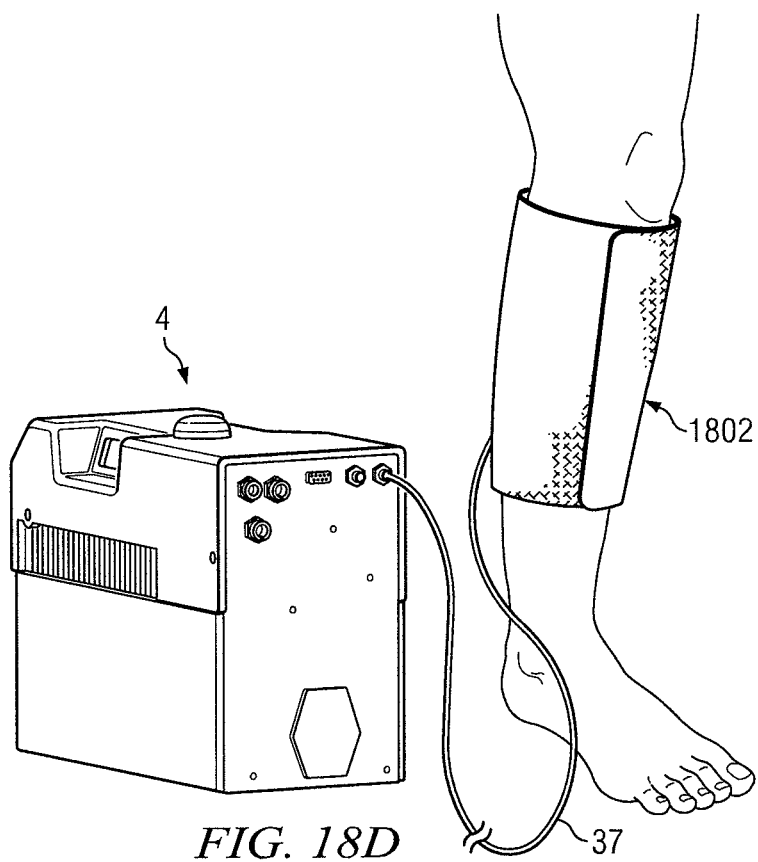

Referring now to FIGS. 18C-18D, operation of the calf wrap 1802 is described. With reference to FIG. 18C, the calf wrap 1802 is positioned on the front side of the calf. Flap 1826 is pulled tight and then flap 1824 is pulled tight overtop and attached. With reference to FIG. 18D, the calf wrap may be connected to the control unit 4 for DVT therapy by connecting DVT connector 37 to inlet 1822. While the embodiment described above pumps gas to provide compression, it is also contemplated that other substances could be utilized to provide the desired compression.

Figure 12:
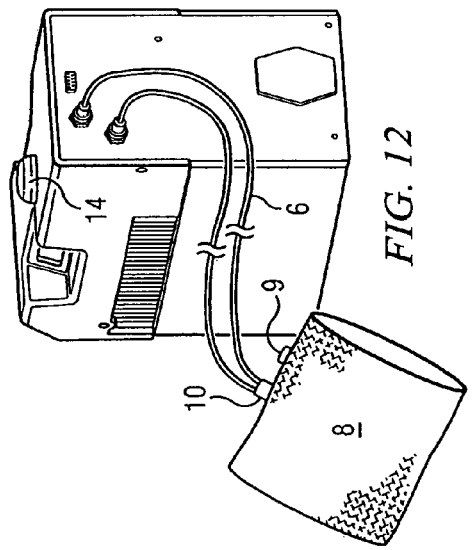
FIG. 12 is a thermal therapy system having a control unit connected to a thermal therapy blanket.

Referring now to FIG. 12, there is shown a thermal therapy device 8 without a tube for delivery of compressed gas. As shown herein, heat transfer fluid flows into the thermal therapy device 8 through an inlet port, and exits through an outlet port to the control unit 4 via connector 10 and connector tubes 6. The control unit 4 and the thermal therapy device 8 may be adapted for the administration of hot, cold, and/or compression therapies to a body portion of the patient. For example, the device 8 may cover different areas of the human body. Current thermal design recommendations for temperature therapy in various embodiments may include one, some, or none of the following: 1) some embodiments are capable of heating the heat transfer fluid from around 37° F. to around 105° F. with a large blanket attached to a typical man (e.g., 5'10" and 180 lbs.) at an ambient of 77° F. within 10 minutes; 2) some embodiments are capable of cooling the heat transfer fluid from around 105° F. to around 49° F. with a large blanket attached to the typical man at an ambient of 77° F. within 20 minutes; and 3) the system may cool the fluid to about 37° F. at an ambient of 77° F. within 90 minutes. These requirements contemplate a compression of approximately 25 mm Hg above ambient or higher. The connector 10 provides a fluid and/or gas connection between the control unit 4 and the thermal therapy device 8 for the transfer of gas and heat transfer fluid. The connector 10 may also allow for transfer of electrical sensor signals and/or data signals between the thermal therapy device 8 and the control unit 4. An emergency relief valve 9 may be utilized to quickly decompress the device 8 if needed.

Figure 13A:
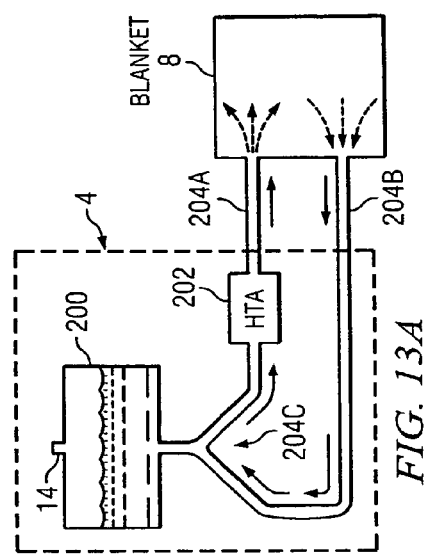
FIG. 13A is a diagrammatic schematic of one aspect of the thermal operation of the thermal therapy system as represented in FIG. 12.

Referring now to FIG. 13A, a block diagram of one embodiment of the flow of heat transfer fluid between the control unit 4 and the thermal therapy device or blanket 8 is illustrated. The control unit 4 includes a heat transfer fluid reservoir 200 and at least one heat transfer assembly (HTA) 202 for heating and/or cooling the heat transfer fluid. Before the blanket 8 is utilized for temperature therapy, the system is primed with the heat transfer fluid. When the system is primed, substantially no gas exists in the tubes 204 between the reservoir 200, HTA 202, and blanket 8. In one embodiment, gas is actively and/or passively removed from the system to ensure substantially no gas exists in the system. The flow tubes in the control unit 4 between the reservoir 200, HTA 202, and blanket 8 form a three-point junction 204C. In one embodiment, the three-point junction 204C is formed as an inverted Y, however, other shapes and orientations are possible. By utilizing a three-point junction 204C, the heat transfer fluid returning from the blanket 8 may be recirculated to the HTA 202 without utilizing heat transfer fluid from the reservoir 200. The three-point junction 204C allows the HTA 202 to heat or cool the heat transfer fluid that has already been heated or cooled prior to entering the blanket 8. In one embodiment, the HTA 202 does not heat or cool the entire contents of the reservoir 200, but merely the portion of the heat transfer fluid that is currently circulating through the blanket 8 and tubing 204. The reservoir may be by-passed unless more fluid volume is needed. In the three-point junction 204C, heat transfer fluid returning from the blanket 8 may be pumped, via a pump, to the HTA 202. If more heat transfer fluid than that which is already circulating through the system is required, then the heat transfer fluid from the reservoir 200 may be introduced into the system. More fluid may be added via opening 14, if needed.

Figure 13C:
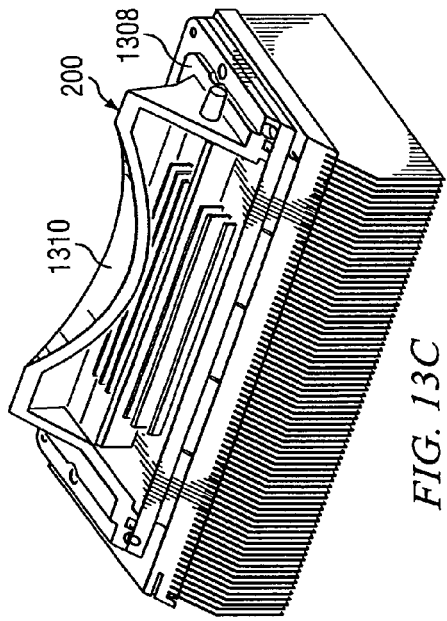
FIG. 13C is a perspective view of an integrated reservoir and HTA according to an embodiment of the present invention.
Figure 13B:
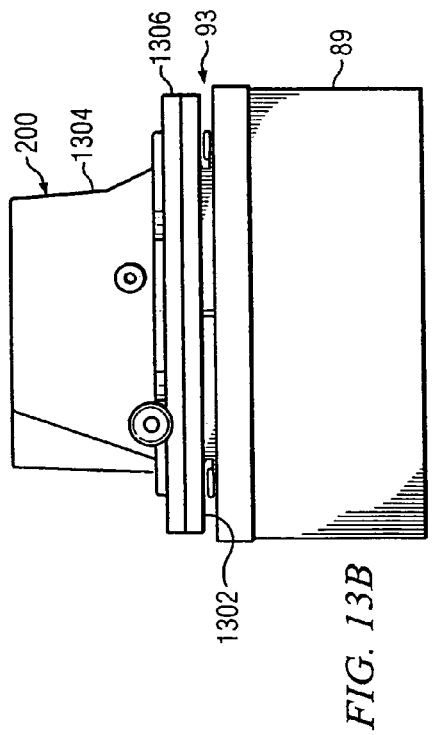
FIG. 13B is a rear view of an integrated reservoir and heat transfer assembly (HTA)

Referring now to FIGS. 13B-13C, the integration of the reservoir 200 and the HTA 202 is illustrated. With reference to FIG. 13B, the rear of the reservoir 200 includes a coolant supply port 1302 for supplying heat transfer fluid to a fluid pump, a coolant return port 1304 for receiving heat transfer fluid from a blanket, and a cold plate 1306. The cold plate 1306 may be positioned at the base of the reservoir 200 and is therefore in direct contact on its underside with the TEC 93. Referring now to both FIGS. 13B and 13C, a divider 1308 is located in the middle of the reservoir 200 between the coolant supply port 1302 and the coolant return port 1304, thereby blocking direct flow of fluid between the two ports. As fluid flows into the back of the reservoir 200 through the coolant return port 1304, the divider 1308 channels the fluid to the front of the reservoir 200 and then back to the coolant supply port 1302. By preventing fluid from short circuiting directly from the coolant return port 1304 to the coolant supply port 1302, the divider 1308 forces exposure of the fluid to the cold/hot plate 1306 which, as a result of its direct contact with the TEC 93, provides a surface area to cool and/or heat the fluid. The reservoir 200 may also includes vertical fins 1310 to further enhance contact areas with the fluid. In one embodiment, the vertical fins may be spaced about 0.5 inches apart and may span the length of the reservoir 200.

Figure 14:
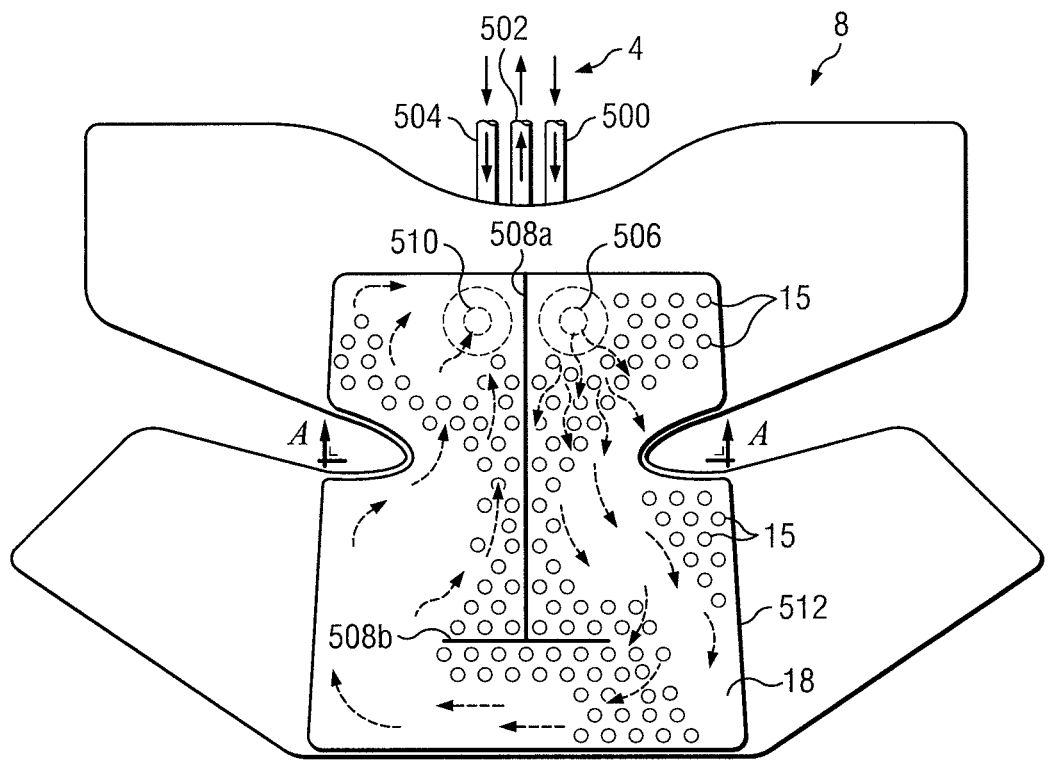
FIG. 14 is a plan view of an embodiment of a thermal therapy blanket.

Referring now to FIG. 14, a temperature therapy blanket 8 having a pre-selected shape and compression capabilities is illustrated. An underside of the blanket 8, as shown, is placed directly against a portion of the patient. The fluid bladder is thus adjacent to the patient. Heat transfer fluid flows into the blanket 8 from inlet hose 500 and heat transfer fluid flows out of the blanket via outlet hose 502. A gas for compression flows into the blanket 8 from gas inlet hose 504. Heat transfer fluid travels through the inlet hose 500, through fluid inlet port 506, and into the blanket 8. Connections 15 connecting the upper and lower layers may be used to force the heat transfer fluid to more evenly disperse throughout the fluid bladder. Partitions 508a, 508b control the flow of heat transfer fluid throughout the fluid bladder. Partition 508a prevents heat transfer fluid from entering the blanket 8 at the inlet port 506 and immediately exiting the blanket via outlet port 510. Partition 508a forces the heat transfer fluid to travel towards the end of the blanket 8 remote from the inlet port 506. Partition 508b, in conjunction with connections 15, causes the heat transfer fluid to travel across the width of the blanket 8. The edges of the fluid bladder are joined to the edges of the gas bladder at seal 512. The heat transfer fluid may then exit the blanket 8 at the outlet port 510. The travel of the heat transfer fluid is indicated by arrows. FIG. 14 shows the configuration of one embodiment, however, various other configurations are contemplated.

Figure 15:
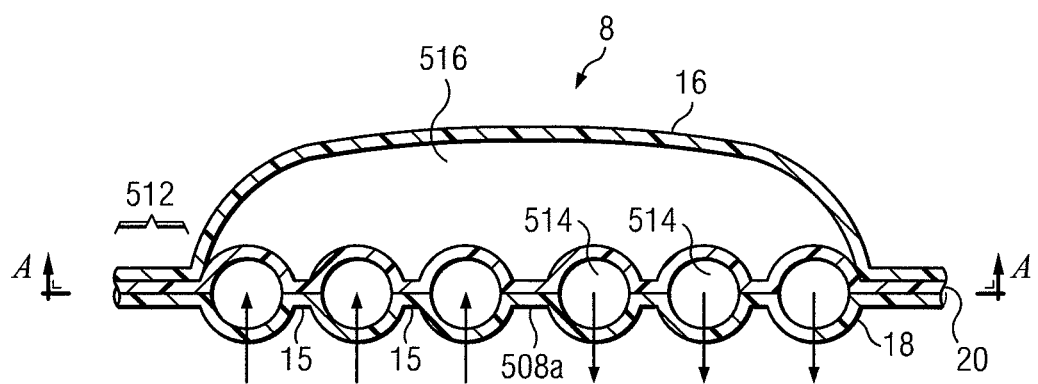
FIG. 15 is a cross-sectional view of the blanket of FIG. 14 illustrating flow of thermal fluid therein and utilization of compression gas thereabove for use in achieving a compression of the thermal fluid against the skin of a patient.
Figure 19:
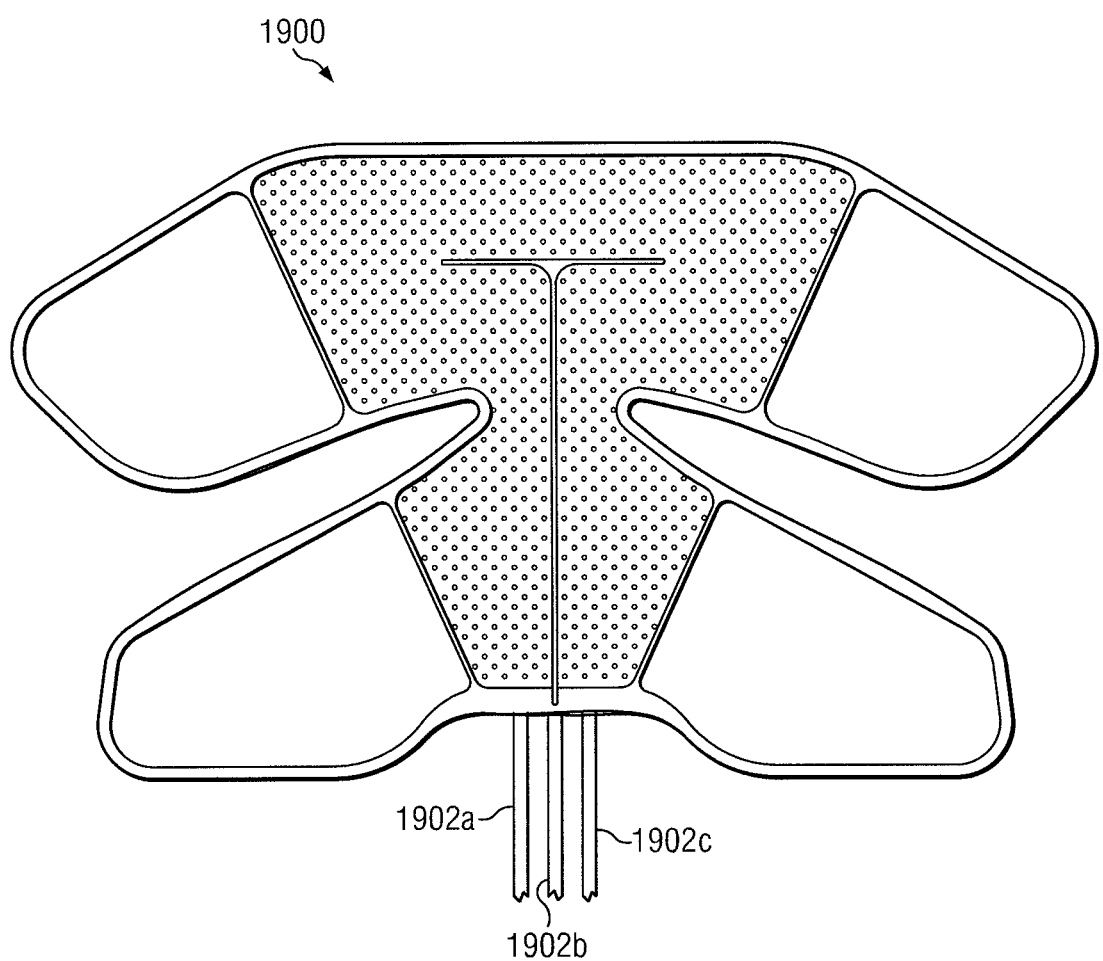
FIG. 19 is a plan view of an embodiment of a thermal therapy blanket.

Referring now to FIG. 15, the blanket 8 is turned over relative to FIG. 14 and a cross-sectional view along line A-A of FIG. 14 is illustrated. As described above, the fluid bladder 514 (disposed against the patient) and the gas bladder 516 are joined together at seal 512. Connections 15 join the upper layer and lower layer of the fluid bladder 514 together. The partition 508a segregates the heat transfer fluid from the inlet port 506, illustrated by downward arrows, from the heat transfer fluid flowing to the outlet port, illustrated by the upward arrows. The gas bladder 516 is oriented over the fluid bladder 514 and serves to press the fluid bladder 514 against a portion of a patient. In another embodiment, the fluid bladder 514 and the gas bladder 516 may have low-profile inline ports such as inline ports 1902(a)-(c) of a temperature therapy blanket 1900 of FIG. 19. Inline ports afford increased comfort to a user by allowing the blanket 8 to lay substantially flat. Embodiments such as the embodiment shown may increase comfort and thereby allow a user to sleep or rest while using the blanket 8.

Figure 16:
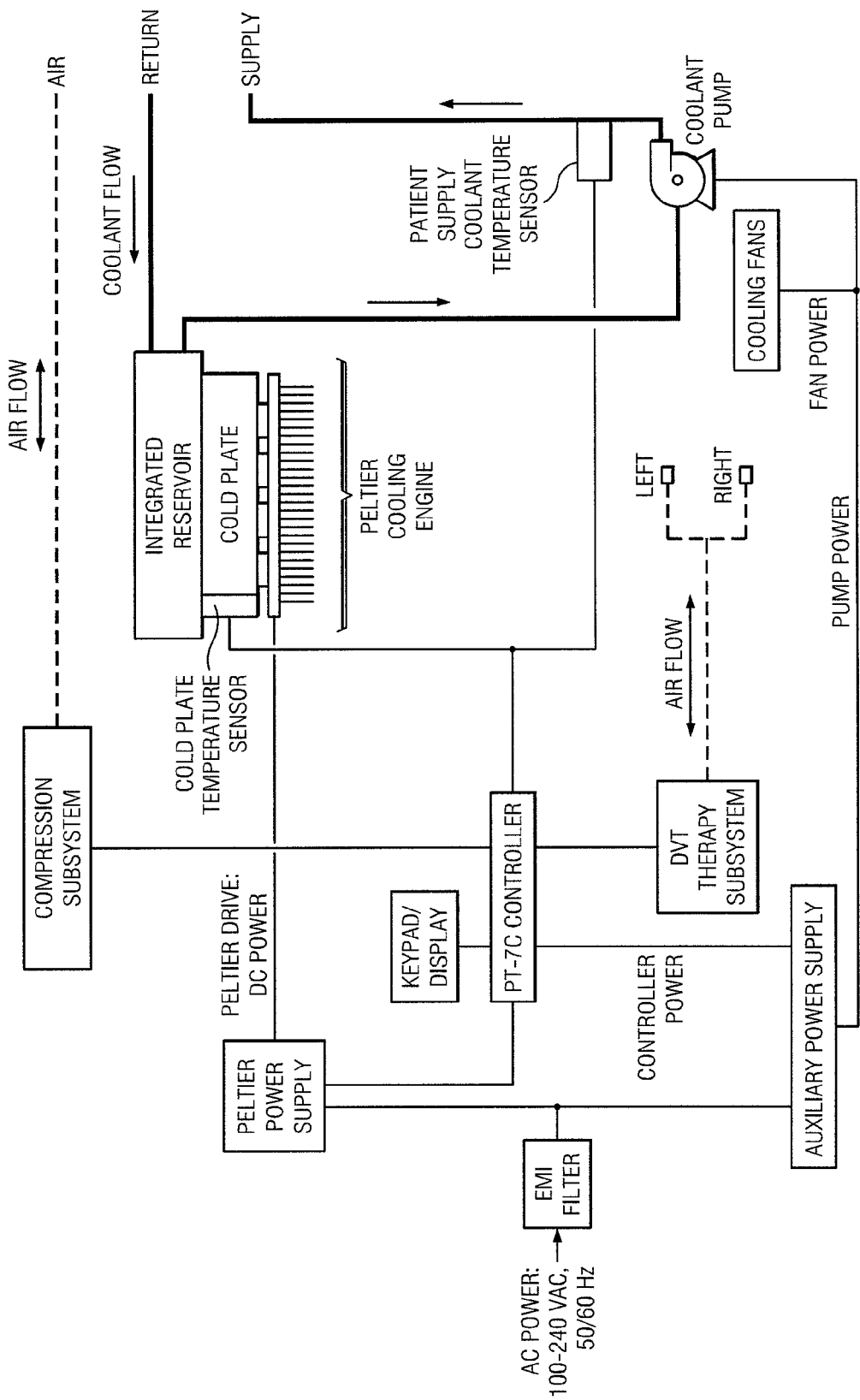
FIG. 16 is a thermal therapy/DVT system block diagram.

Referring now to FIG. 16, there is shown a thermal therapy/DVT system block diagram where gas is provided in a compression subsystem in conjunction with Peltier cooling of a fluid for thermal therapy. The coolant flow may be thermally conditioned by the Peltier cooling engine. Patient supply cooling temperature sensors are utilized in conjunction therewith. Coolant pumps are utilized in conjunction with cooling fans. The cooling fans, as described above, provide selective cooling in a manner most efficient for the construction and operation of the control unit.

Still referring to FIG. 16, the Peltier power supply is shown to be controlled by a PT-7C controller accessed via a keypad display. Various other features for control and power supply have likewise been included, such as an electro-magnetic interference (EMI) filter and auxiliary power supply used in conjunction with the DVT therapy subsystem. It may be seen that the DVT therapy subsystem provides a separate gasflow for both left and right applications for utilization in DVT treatment of a patient.

Figure 17:
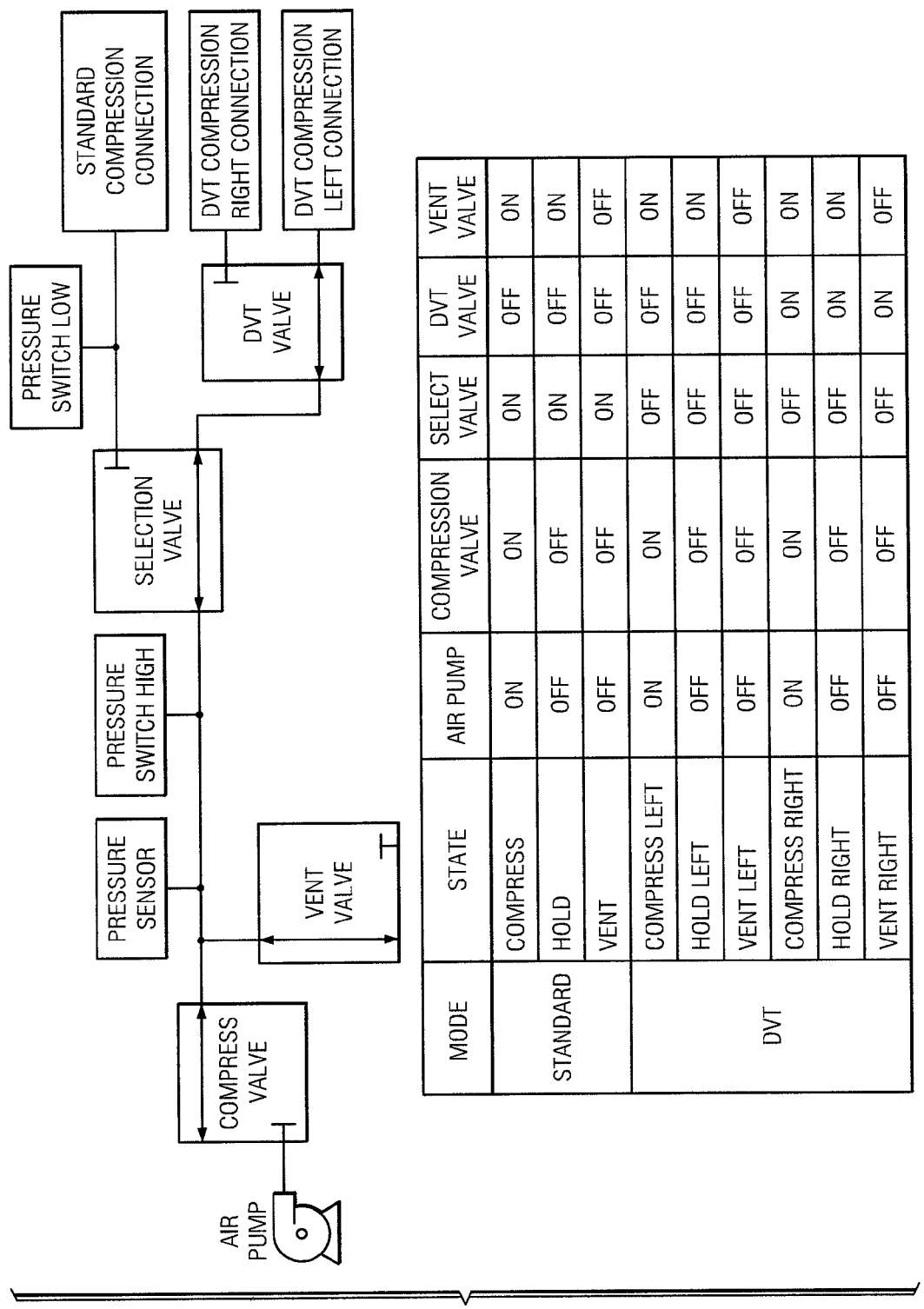
FIG. 17 is a DVT therapy block diagram further illustrating the operation thereof.

Referring now to FIG. 17, there is shown a DVT therapy block diagram where the gas pump is shown to be in flow communication with a compress valve utilized with a vent valve and a pressure sensor in association with a pressure switch high and pressure switch low. The various modes of operation utilizing gas pump, compression valve, select valve, DVT valve, and vent valve are shown. In various embodiments, sequenced compression may also be utilized in combination with standard compression.

The previous description is of embodiments of the invention. The scope of the invention should not necessarily be limited by this description. The scope of the present invention is instead defined by the following claims.

What is claimed is:

1. A system for addressing deep-vein-thrombosis (DVT) in a patient utilizing compression therapy, the system comprising:
 a control unit for thermally conditioning a heat-transfer liquid to a predetermined temperature and providing a compressed gas at one or more predetermined pressures;
 a thermal therapy pad coupled to the control unit and that conducts the heat-transfer liquid therethrough;
 a compression therapy device comprising a bladder and disposed outwardly of the thermal therapy pad, the compression therapy device being coupled to the control unit to receive at least a portion of the compressed gas to fill the bladder and to compress the thermal therapy pad against a first portion of a first extremity of the patient;
 a first DVT compression device coupled to the control unit and that receives a first pulse of compressed gas from the control unit, the first DVT compression device adapted for securement to and compression of a second portion of the first extremity of the patient;
 a second DVT compression device coupled to the control unit and that receives a second pulse of compressed gas from the control unit, the second DVT compression device adapted for securement to and compression of a portion of a second extremity of the patient;
 wherein the control unit provides the first pulse only when the compressed gas is not being applied to the compression therapy device.

2. The system of claim 1, wherein the thermal therapy pad and the compression therapy device are integrated into a single device.

3. The system of claim 1, wherein compressed gas is provided to the first DVT compression device during the first pulse for a user-specified length of time and compressed gas is provided to the second DVT compression device during the second pulse for a user-specified length of time.

4. The system of claim 1, wherein the control unit is adapted to provide the compressed gas to the compression therapy device, the first DVT compression device, and the second DVT compression device at one or more user-specified pressures.

5. The system of claim 1, wherein the second portion of the first extremity of the patient is a first foot of the patient and the portion of the second extremity of the patient is a second foot of the patient.

6. The system of claim 1, wherein the second portion of the first extremity of the patient is a first calf of the patient and the portion of the second extremity of the patient is a second calf of the patient.

7. The system of claim 1, wherein the first portion of the first extremity of the patient is a knee of the patient.

8. The system of claim 1, wherein the control unit is adapted to provide compressed gas to three or more bladders disposed within the compression therapy device.

9. The system of claim 8, wherein the control unit is adapted to cycle through the following:
- provide a pulse of compressed gas to a first bladder of the compression therapy device;
- provide a pulse of compressed gas to a second bladder of the compression therapy device; and
- provide a pulse of compressed gas to a third bladder of the compression therapy device.

10. A system for addressing deep-vein-thrombosis (DVT) in a patient utilizing compression therapy, the system comprising:
- a control unit for thermally conditioning a heat-transfer liquid to a predetermined temperature and providing compressed gas at a predetermined pressure in a select order;
- a thermal compression therapy device coupled to the control unit and adapted for securement to the patient, the thermal compression therapy device receiving both at least a portion of the heat-transfer liquid and at least a portion of the compressed gas to compress the thermal therapy device against a first portion of a first extremity of the patient;
- a first DVT compression device coupled to the control unit and adapted for securement to the patient, the first DVT compression device receiving a first pulse of compressed gas from the control unit to compress a second portion of the first extremity of the patient;
- a second DVT compression device coupled to the control unit for securement to the patient, the second DVT compression device receiving a second pulse of compressed gas from the control unit to compress a portion of a second extremity of the patient;
- wherein the control unit provides the first pulse to the first DVT compression device only when the compressed gas is not being applied to the thermal compression therapy device.

11. The system of claim 10, wherein the thermal therapy device and the compression therapy device are integrated into a single device adapted for application to the knee of the patient.

\* \* \* \* \*

UNITED STATES PATENT AND TRADEMARK OFFICE
CERTIFICATE OF CORRECTION

PATENT NO. : 8,778,005 B2
APPLICATION NO. : 12/234394
DATED : July 15, 2014
INVENTOR(S) : Overton L. Parish et al.

Page 1 of 1

It is certified that error appears in the above-identified patent and that said Letters Patent is hereby corrected as shown below:

On the title page, item 60

Replace "Provisional application No. 60/791,132, filed on Apr. 11, 2006, provisional application No. 60/817,932, filed on Jun. 30, 2006, provisional application No. 60/488,709, filed on Jul. 18, 2003, provisional application No. 60/550,658, filed on Mar. 5, 2004, provisional application No. 60/588,453, filed on Jul. 6, 2004." with -- Provisional application No. 60/791,132, filed on Apr. 11, 2006, provisional application No. 60/817,932, filed on Jun. 30, 2006, provisional application No. 60/488,709, filed on Jul. 18, 2003, provisional application No. 60/550,658, filed on Mar. 5, 2004, provisional application No. 60/588,453, filed on Jul. 16, 2004. --

Signed and Sealed this
Fourteenth Day of June, 2016

Michelle K. Lee
*Director of the United States Patent and Trademark Office*